United States Patent
Ramamoorthy

(10) Patent No.: US 12,426,842 B2
(45) Date of Patent: Sep. 30, 2025

(54) METHODS AND SYSTEMS FOR FLEXIBLE PADDLE FOR USE WITH A MAMMOGRAPHY SYSTEM

(71) Applicant: GE Precision Healthcare LLC, Wauwatosa, WI (US)

(72) Inventor: Govindh Ramamoorthy, Bangalore (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 283 days.

(21) Appl. No.: 18/186,026

(22) Filed: Mar. 17, 2023

(65) Prior Publication Data
US 2024/0307010 A1    Sep. 19, 2024

(51) Int. Cl.
*A61B 6/04* (2006.01)
*A61B 6/50* (2024.01)

(52) U.S. Cl.
CPC ........... *A61B 6/0414* (2013.01); *A61B 6/502* (2013.01)

(58) Field of Classification Search
CPC ........... A61B 6/00; A61B 6/04; A61B 6/0414; A61B 6/0435; A61B 6/502
See application file for complete search history.

(56) References Cited

U.S. PATENT DOCUMENTS

| | | | |
|---|---|---|---|
| 6,999,553 B2 | 2/2006 | Livingston | |
| 10,905,385 B2 | 2/2021 | DeFreitas et al. | |
| 11,364,000 B2 | 6/2022 | Defreitas et al. | |
| 2002/0061090 A1 | 5/2002 | Lindstrom | |
| 2017/0042491 A1 | 2/2017 | Yoon | |
| 2020/0093440 A1 | 3/2020 | Small et al. | |

OTHER PUBLICATIONS

EP application 24159689.9 filed Feb. 26, 2024—Search Report issued Jun. 27, 2024; 10 pages.

*Primary Examiner* — Jurie Yun
(74) *Attorney, Agent, or Firm* — McCoy Russell LLP

(57) ABSTRACT

Various methods and systems are provided for a flexible paddle which provides breast positioning assistance during mammography procedures. In one example, the flexible paddle comprises a paddle frame having a cutout at an end of each of a first arm and a second arm, the cutout extending into a width, perpendicular to a length, of each of the first arm and the second arm, and a paddle plate having a projection positioned in a mid-region of each of a first side and a second side, the projection extending into the respective cutout of the paddle frame and coupled to the paddle frame by a plurality of compliant mechanisms to form a compliant, non-sliding, rotationally-flexible hinge.

20 Claims, 16 Drawing Sheets

METHODS AND SYSTEMS FOR FLEXIBLE PADDLE FOR USE WITH A MAMMOGRAPHY SYSTEM

FIELD

Embodiments of the subject matter disclosed herein relate to mammography procedures, and more particularly, to breast positioning assistance for workflow and user/patient experience improvement during mammography procedures.

BACKGROUND

Mammography is a medical imaging procedure for diagnosing one or more conditions of a breast, such as cancer or other diseases. Accurate interpretation of a mammography image (also known as mammogram) and resulting diagnosis relies on generation of high quality mammograms. A key factor affecting the quality of a mammogram is breast positioning. Improper positioning of the breast may result in mammographic artifacts and tissue exclusion, and consequently, missed or inaccurate diagnoses. The level of training and experience of the technologists can significantly affect image quality. For example, technologists with less/intermediate training and/or experience may not position the breast properly, and as result, recall rates and missed diagnoses may be higher. Additionally, breast positioning includes compression of the breast, which may provide further challenges in breast positioning, such as discomfort experienced by the patient which may lead to movement before and/or during image capture.

BRIEF DESCRIPTION

Described herein is a flexible paddle which may be used with a mammography system to compress a breast for mammography procedures. The flexible paddle includes a paddle frame having a cutout at an end of each of a first arm and a second arm, the cutout extending into a width of each of the first arm and the second arm. The flexible paddle further includes a paddle plate having a projection positioned in a mid-region of each of a first side and a second side, the projection extending into the respective cutout of the paddle frame and coupled to the paddle frame by a plurality of elastically deformable compliant mechanisms to form a compliant, non-sliding, rotationally-flexible hinge. A compliant mechanism may be defined as a flexible mechanism that achieves force and motion transmission through elastic body deformation. During operation of the mammography system, the flexible paddle may be removably coupled to a compression arm assembly of the mammography system. The compression arm assembly is configured to move linearly towards a support platform on which a breast is positioned. When the paddle plate is in at least partial contact with the breast and the compression arm assembly has linear, downward movement, the plurality of compliant mechanisms of the flexible paddle elastically deform (e.g., rotationally contract), enabling the paddle plate to tilt relative to the paddle frame, which is substantially horizontal. In this way, the breast may be compressed while alleviating some of the compressive force from the flexible paddle on portions of the breast for which compression is not desired. By using the plurality of compliant mechanisms to enable tilting of the paddle plate, a weight and complexity of the flexible paddle may be reduced, compared to conventional compression paddles which include many parts, such as a series of elastomers, springs, and/or motors to tilt a paddle plate relative to a paddle frame.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
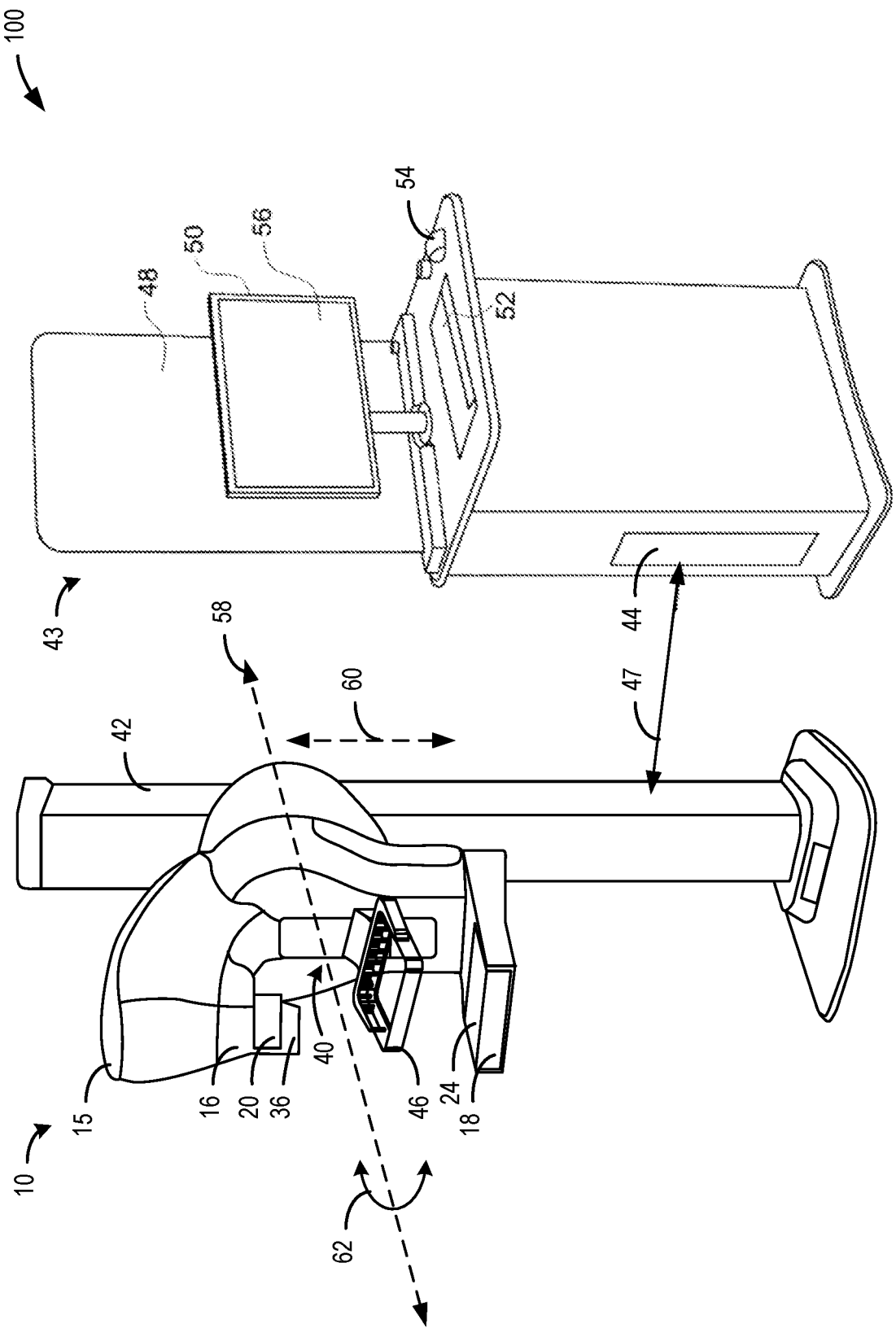
FIG. 1 is a schematic illustration of a mammography system, according to an embodiment of the disclosure.

The following description relates to various embodiments for a flexible paddle which may be used in an x-ray system for mammography procedures to compress a breast. During an imaging procedure, such as mammography or digital breast tomosynthesis (DBT) imaging procedure, and during an image-guided interventional procedure, such as DBT-guided biopsy, contract enhanced spectral mammography (CESM) biopsy, stereotactic biopsy, etc., positioning the breast properly influences a quality of obtained images that demonstrate the various areas of the breast.

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the imaging plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view. Compression paddles are typically manufactured from a clear, rigid material that enables a technical operating a breast imaging system to view the breast at various points during breast positioning and imaging. This allows the technician to properly access the breast, for example, to avoid wrinkles in the tissue, to properly position the nipple, and so on. Compression paddles may be formed of hard plastic such that compression force applied by the compression paddle may effectuate full compression to completely flatten the breast.

One known challenge in mammography and breast tomosynthesis is the discomfort the patient may feel when the breast is compressed, which is done with force sufficient to immobilize the breast and spread out the breast tissues for x-ray imaging. Discomfort may potentially cause the patient to move, which negatively impacts image quality. Discomfort may also potentially dissuade patients from getting screened for breast cancer. Another known challenge is to ensure that the imaged field includes the desired amount of breast tissue.

Some mammography systems may use a flexible compression paddle comprising a paddle plate which is tilted relative to the breast support platform during compression. Clinically, tilting of the paddle plate helps to increase patient comfort during compression by alleviating some of the compressive force on the breast when the paddle plate tilts upwards. In previous example flexible compression paddle designs, tilting of the paddle plate is achieved by an assembly of the flexible compression paddle including a tilt frame, a fixed frame, and a series of elastomers between the tilt frame and the fixed frame. Some flexible compression paddles have a flex mechanism with several parts to enable flexibility, however the inclusion of several parts may make the compression paddle heavy and expensive to produce.

It is desirable to reduce complexity of the flexible compression paddle, which may assist in reducing a part cost and a weight of the flexible compression paddle. In some examples, the part cost for the flexible compression paddle may be reduced by creating a paddle which is entirely formed of plastic (e.g., no metal springs or elastomers in a flex mechanism of the flexible compression paddle). However, there exist challenges in creating a plastic flexible compression paddle which is capable of the tilting motion performed by existing flexible compression paddles (e.g., with flex mechanisms as described above). There exist compression paddles which are formed of plastic, however conventional plastic compression paddles may be formed of many individual parts which may be assembled prior to use. Assembly of parts for plastic flexible compression paddles is undesirable, as multiple parts increase a complexity of the flexible compression paddle as well as time and resources used to create the compression paddle. It is preferable for the plastic flexible compression paddle to be formed using a single injection mold. Further, it is desirable that a hinge point (e.g., position of a flexible mechanism) of the plastic flexible compression paddle is provided at a current hinge point of conventional flexible compression paddles (e.g., provide a flex mechanism for the plastic paddle at the same location where the flex mechanism is positioned on the flex paddle) without requiring an assembly which has multiple parts.

The inventors herein have identified the above-mentioned issues and provide methods and systems for improving positioning of breast prior to initiating acquisition. In particular, methods and systems are provided for a flexible paddle which may be removably coupled to an x-ray system for mammography and biopsy procedures. The flexible paddle is comprised of a paddle frame which is coupled to a paddle plate by a plurality of compliant mechanisms to form a compliant, non-sliding, rotationally-flexible hinge that enables tilting of the paddle plate relative to the paddle frame by elastic deformation of the compliant mechanisms when the paddle plate is engaged with a breast positioned on the breast support. The hinge gains some or all of its motion from a relative flexibility of the compliant mechanisms, rather than from rigid body joints, and provides biasing torque/force to the paddle, thus reducing a complexity and weight of the flexible compression paddle. Elastic deformation of the compliant mechanisms enables the compliant mechanisms to transition from a relaxed configuration (e.g., when the paddle plate is not engaged) to a contracted configuration (e.g., when the paddle plate is engaged), and return to the relaxed configuration (e.g., when the paddle plate is not engaged) without undesired deformation of the compliant mechanisms (e.g., in a contracted configuration when a relaxed configuration is desired).

Figure 2:
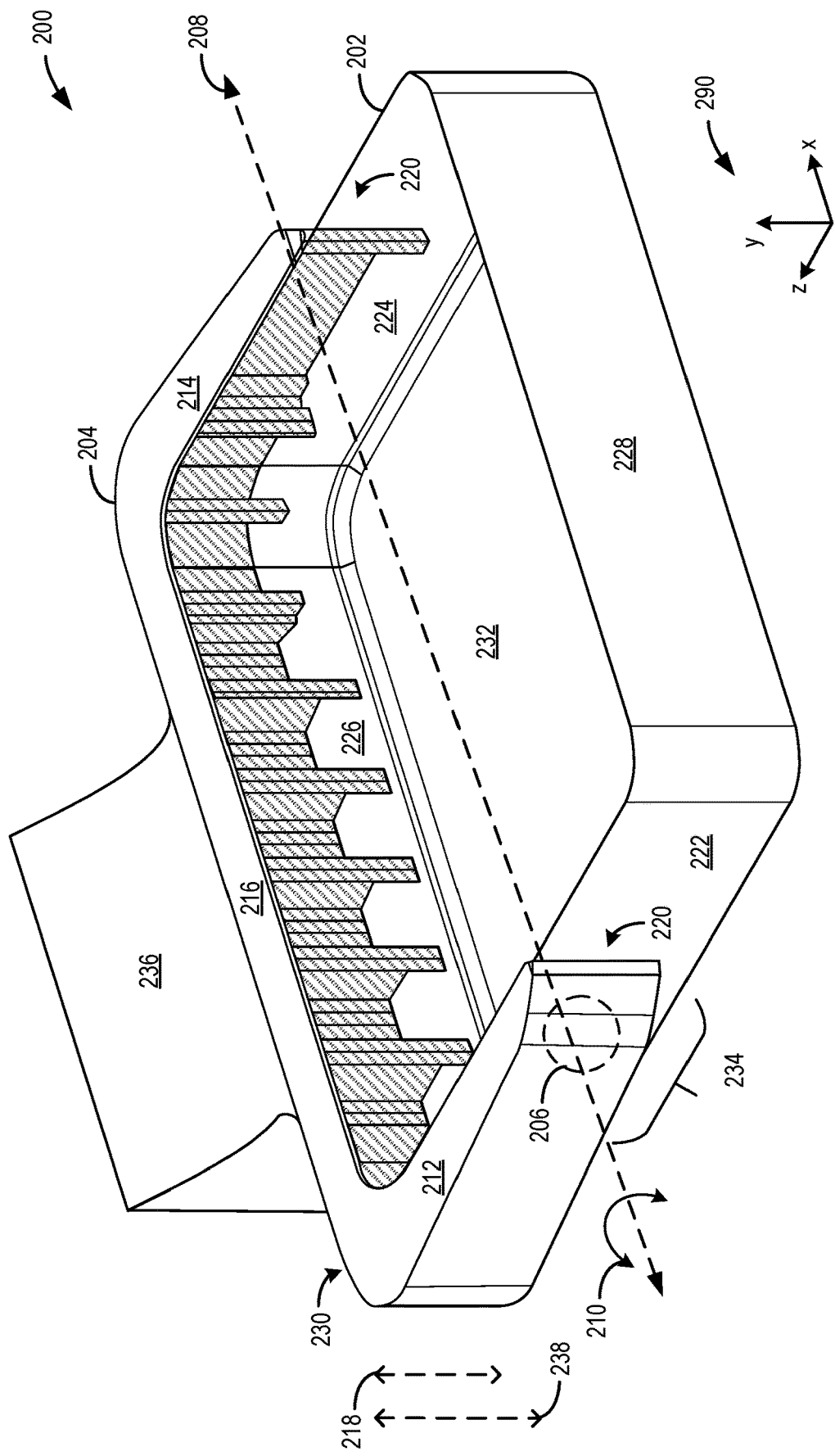
FIG. 2 shows a first embodiment of a flexible paddle which may be used with the mammography system of FIG. 1.
Figure 3:
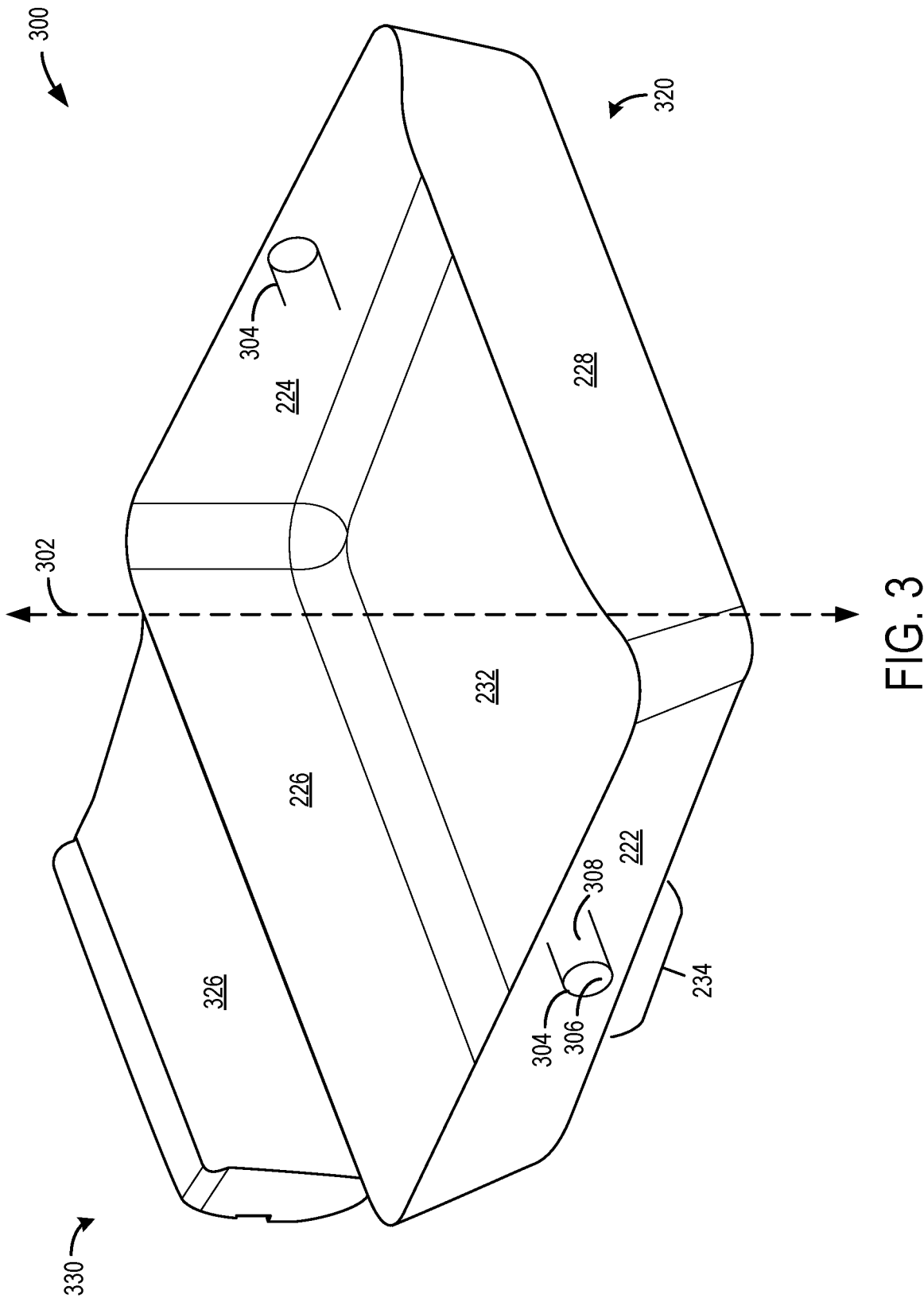
FIG. 3 shows a first example of a paddle plate which may be included in the flexible paddle of FIG. 2.
Figure 4:
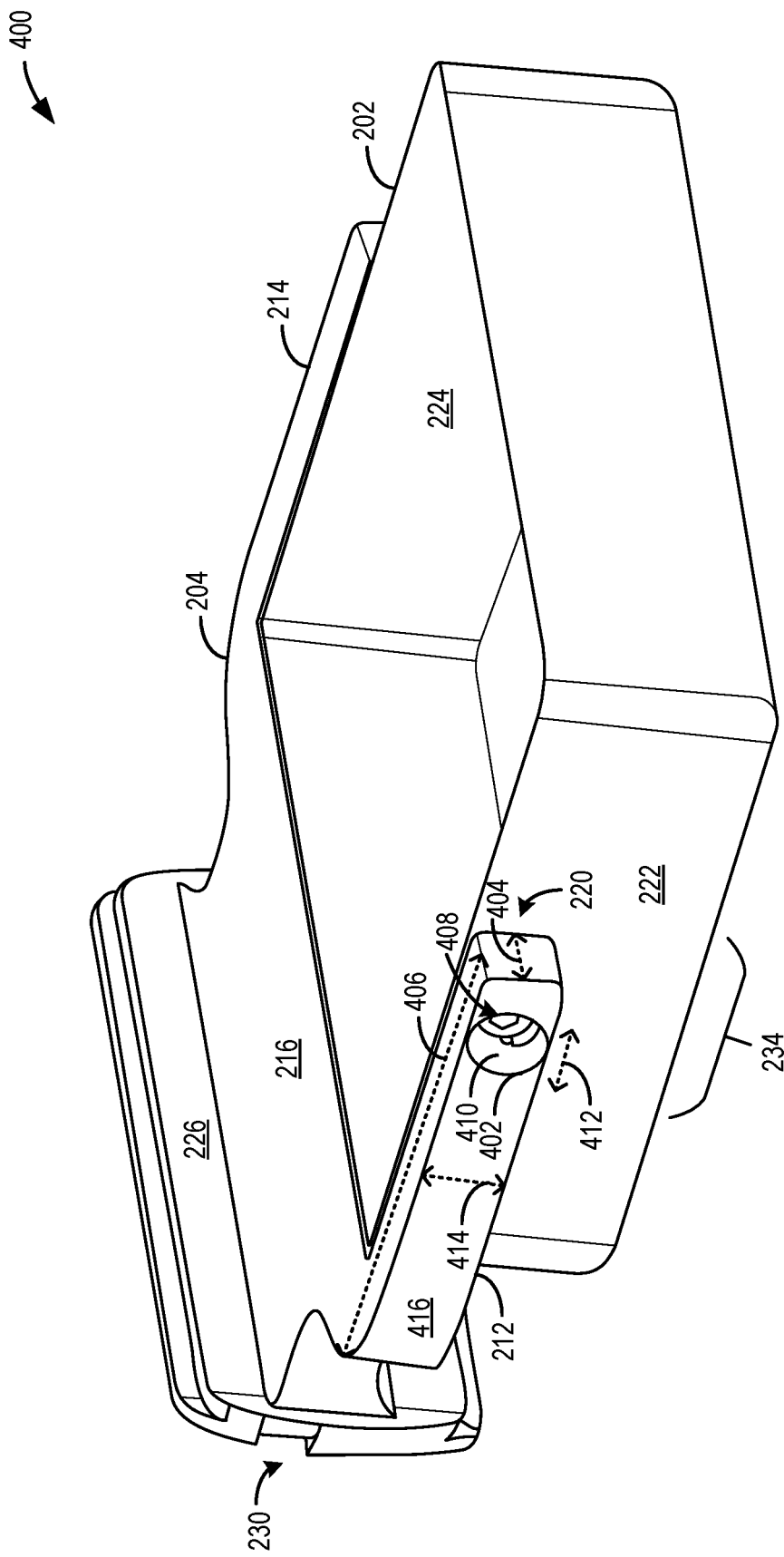
FIG. 4 shows a second embodiment of a flexible paddle which may be used with the mammography system of FIG. 1.
Figure 5A:
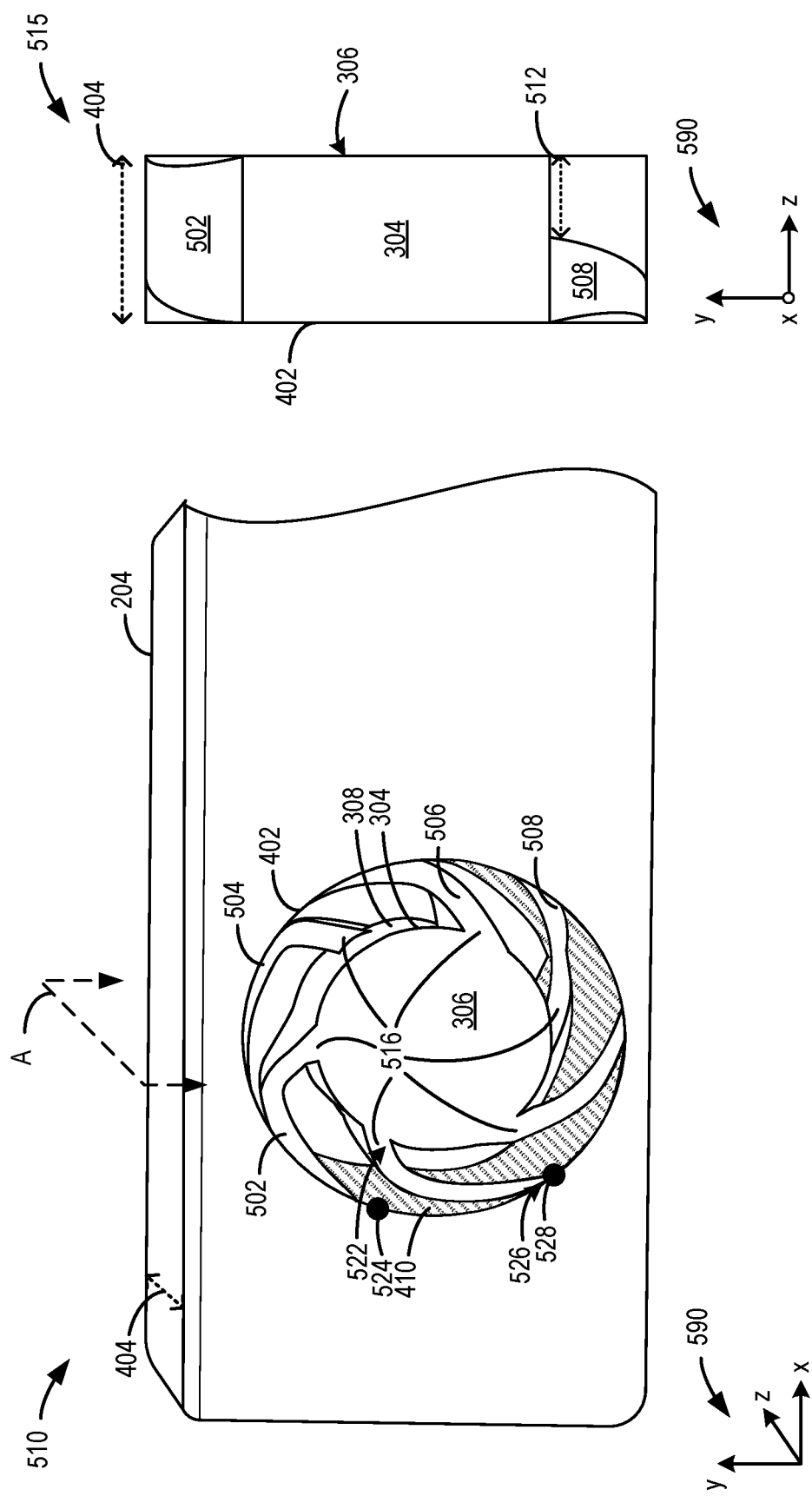
FIG. 5A shows a first embodiment of a compliant, non-sliding, rotationally-flexible hinge for a flexible paddle.
Figure 5B:
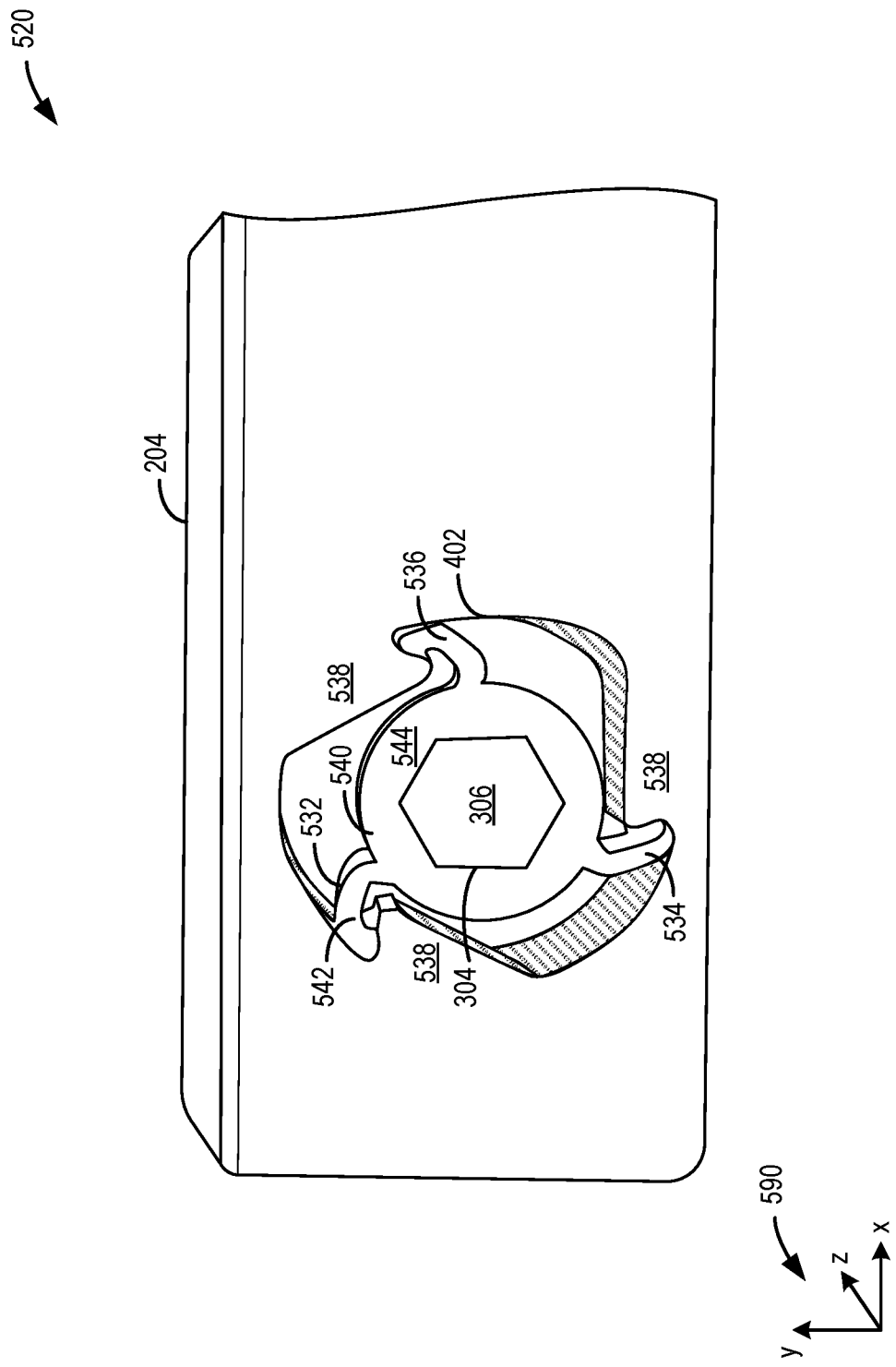
FIG. 5B shows a second embodiment of a compliant, non-sliding, rotationally-flexible hinge for a flexible paddle.
Figure 5C:
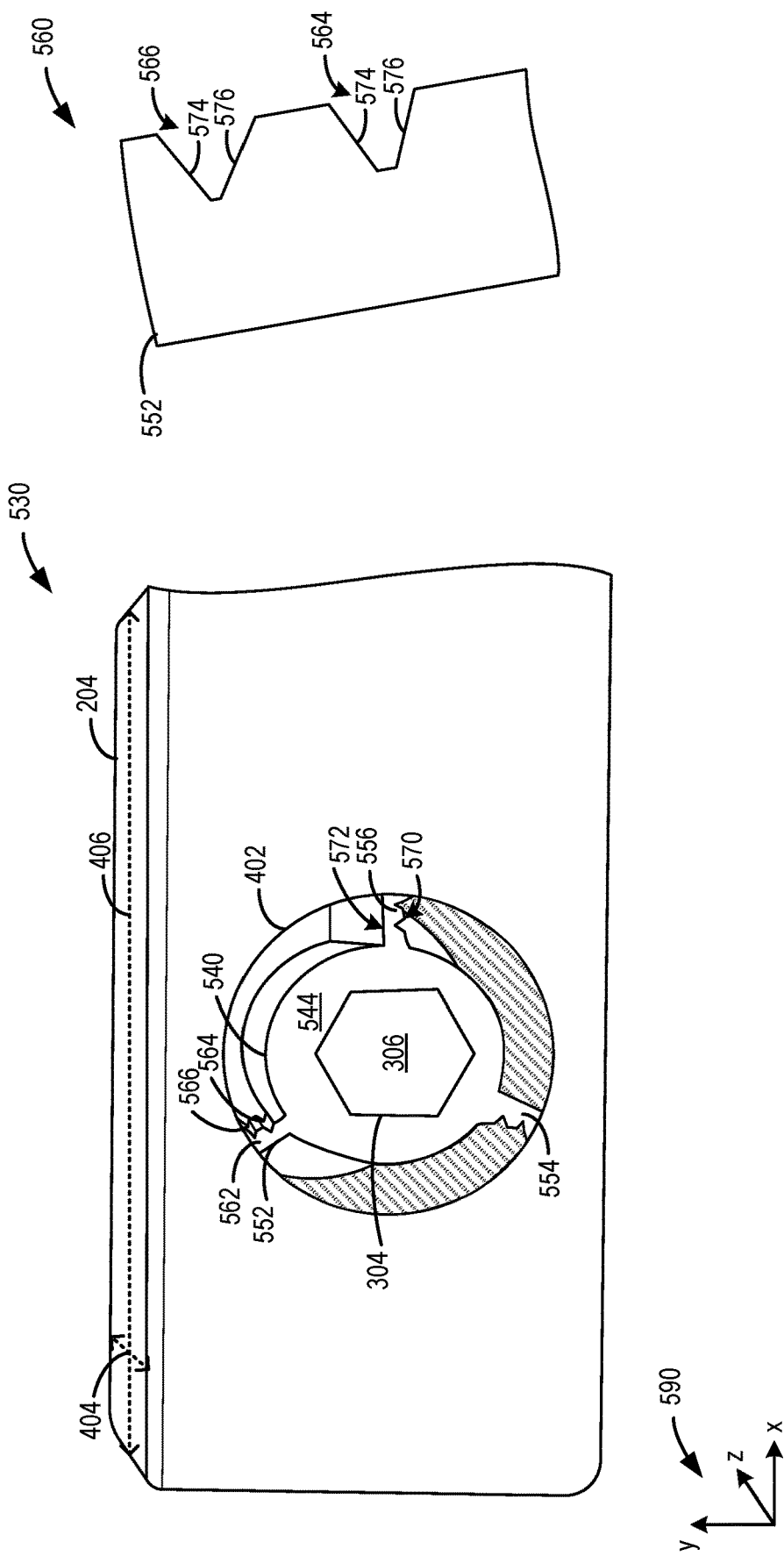
FIG. 5C shows a third embodiment of a compliant, non-sliding, rotationally-flexible hinge for a flexible paddle.
Figure 6A:
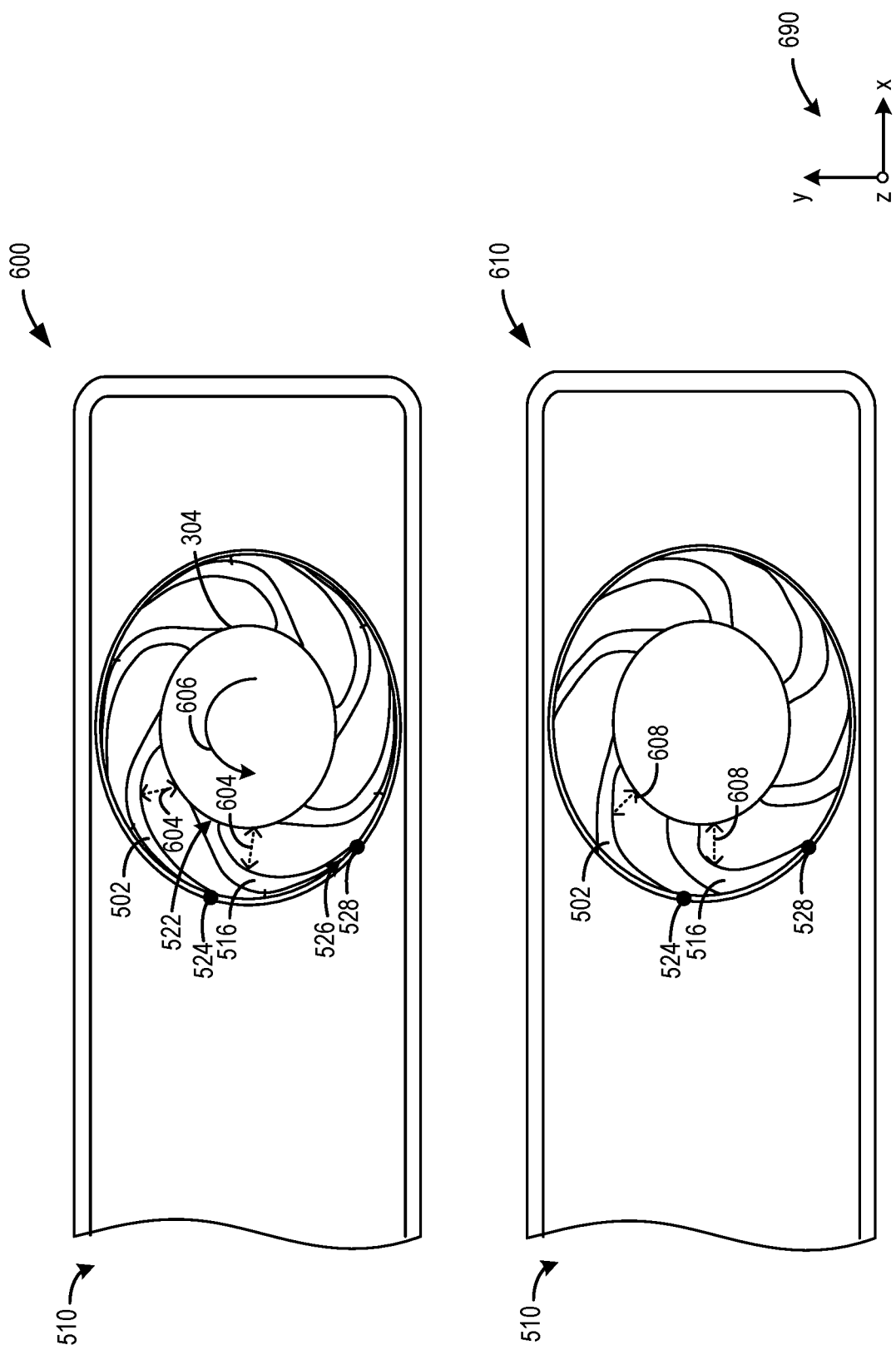
FIG. 6A shows the first embodiment of the hinge of FIG. 5A in a relaxed configuration and in an elastically deformed configuration.
Figure 6B:
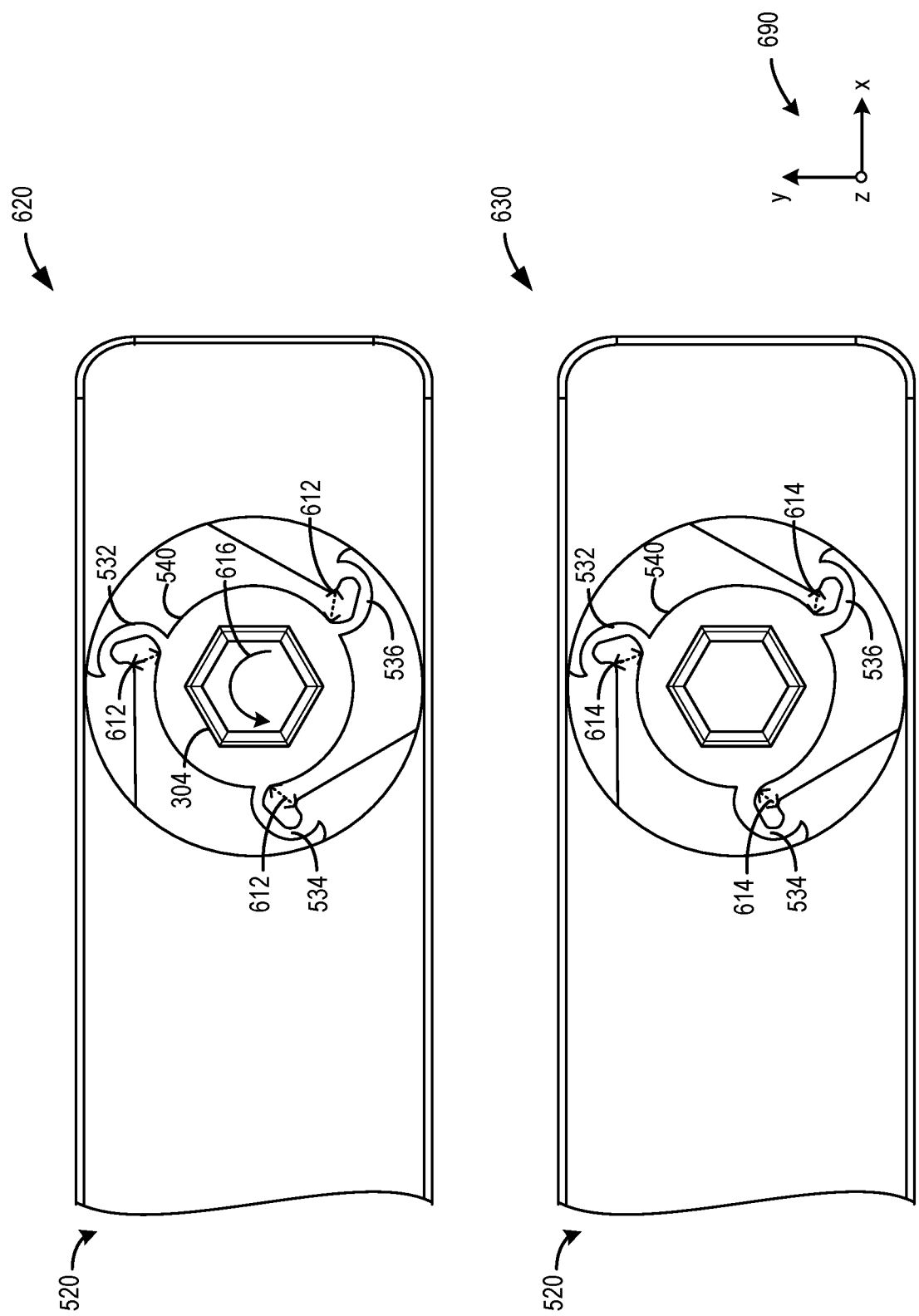
FIG. 6B shows the second embodiment of the hinge of FIG. 5B in a relaxed configuration and in an elastically deformed configuration.
Figure 6C:
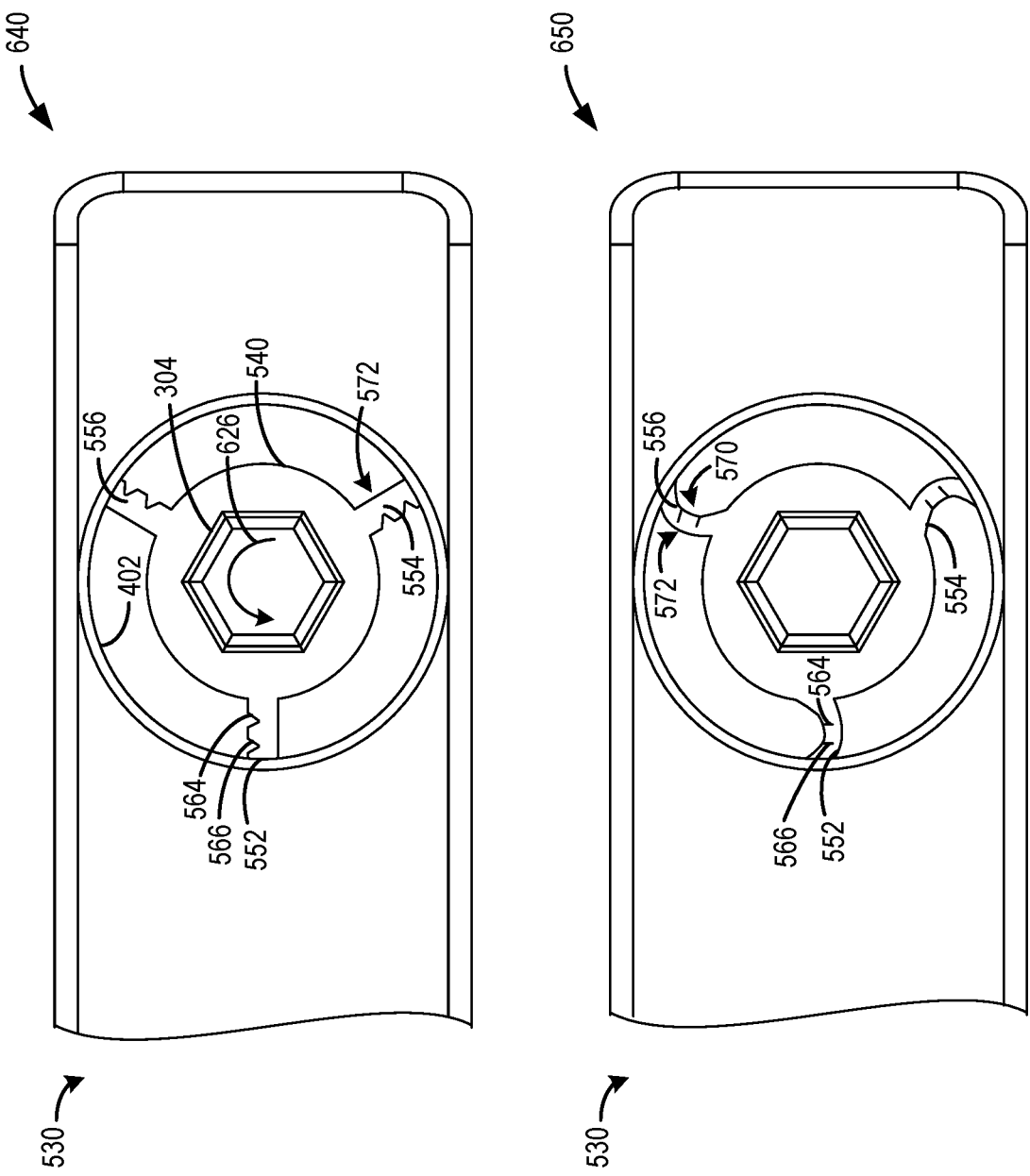
FIG. 6C shows the third embodiment of the hinge of FIG. 5C in a relaxed configuration and in an elastically deformed configuration.
Figure 7:
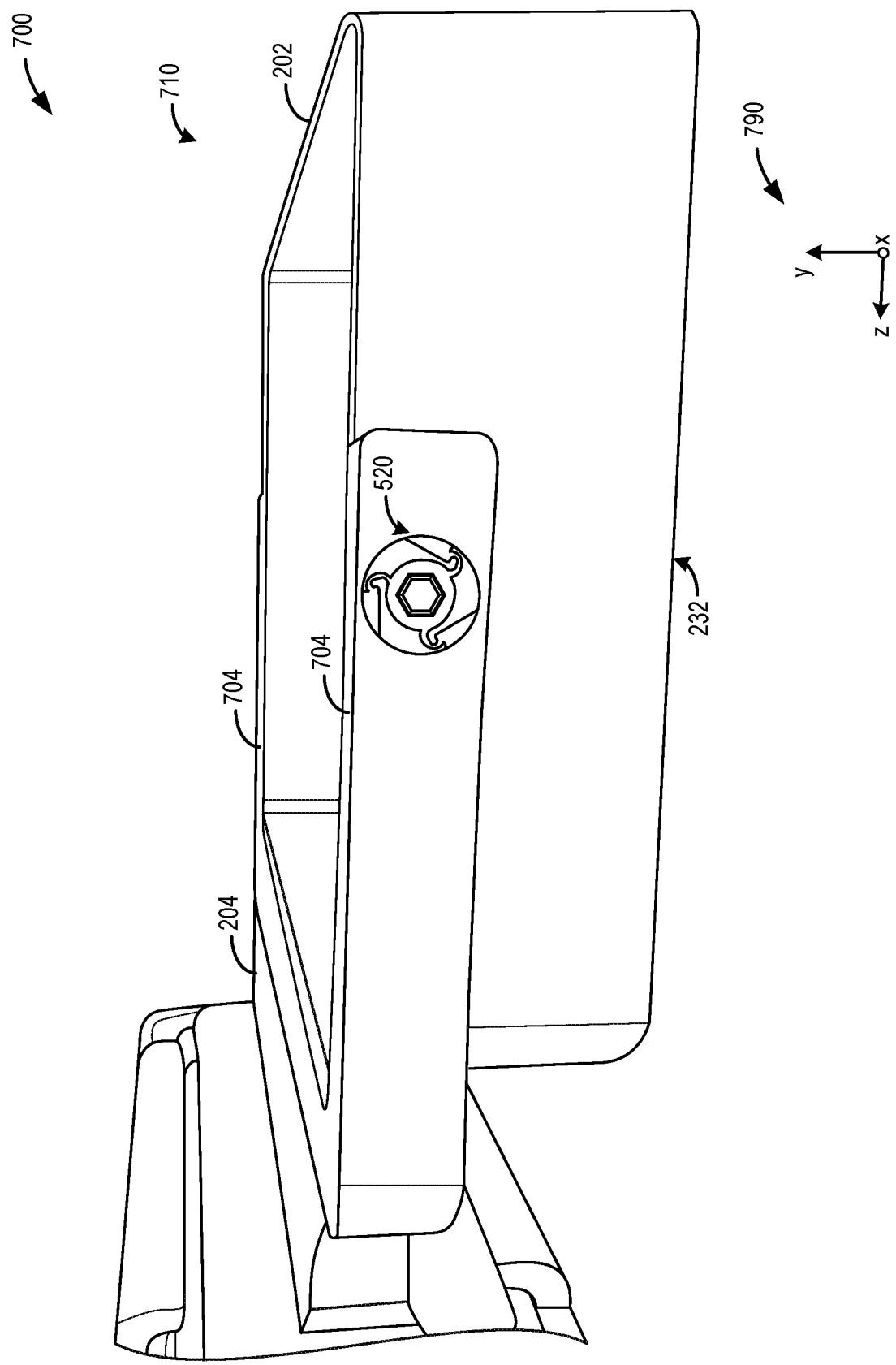
FIG. 7 shows the flexible paddle of FIG. 4 in an untilted configuration.
Figure 8:
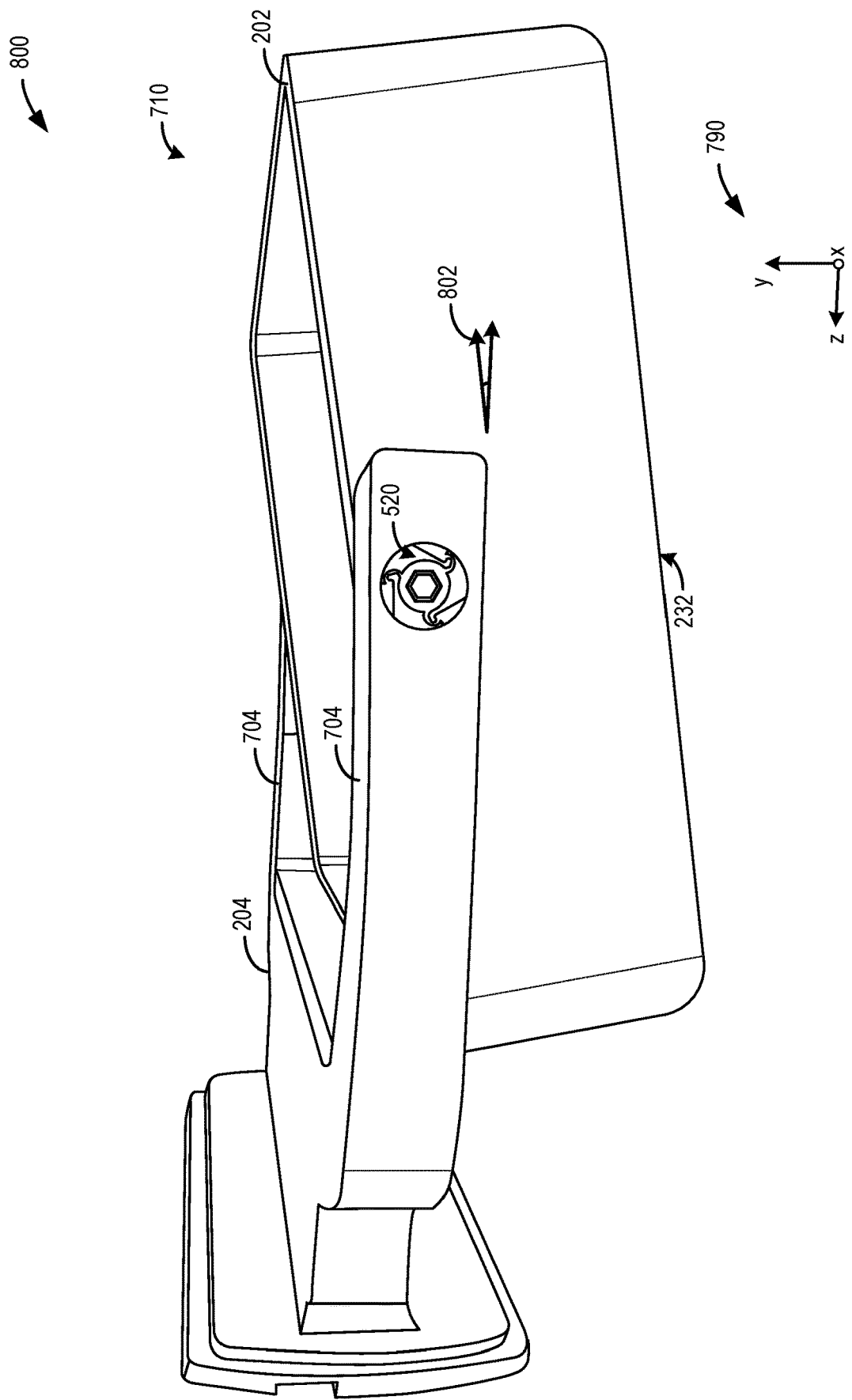
FIG. 8 shows the flexible paddle of FIG. 4 in a tilted configuration.
Figure 9A:
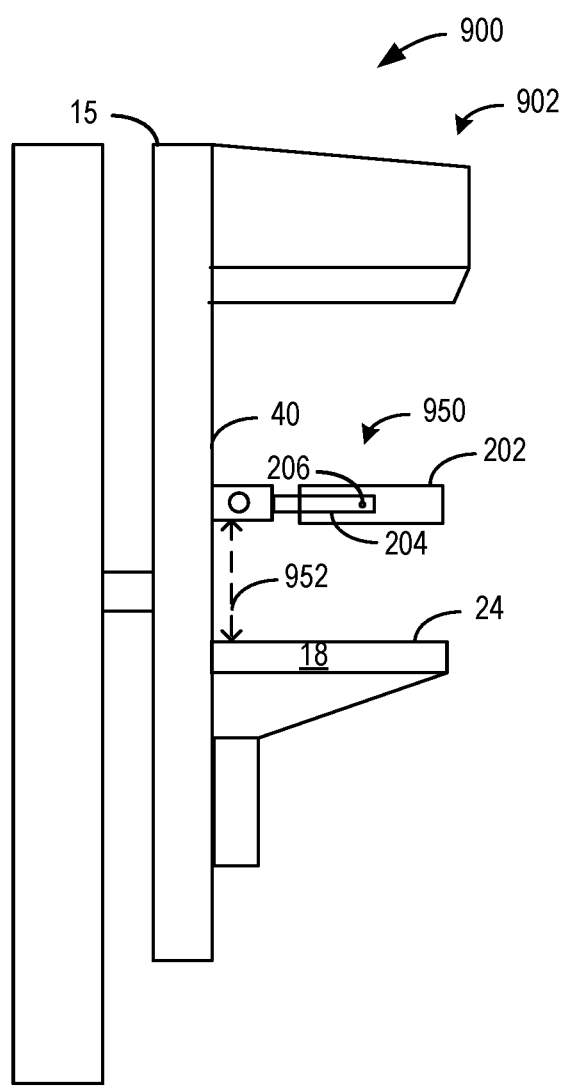
FIG. 9A shows the mammography system of FIG. 1, including a flexible paddle, in a procedure-ready condition.
Figure 9B:
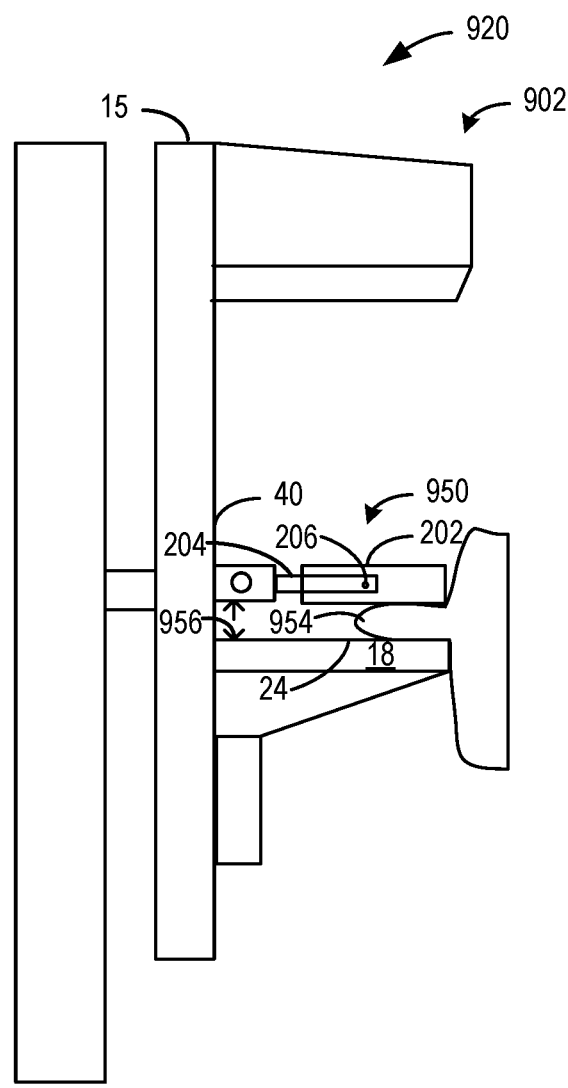
FIG. 9B shows the mammography system of FIG. 1, including a flexible paddle, in a compression-ready condition.
Figure 9C:
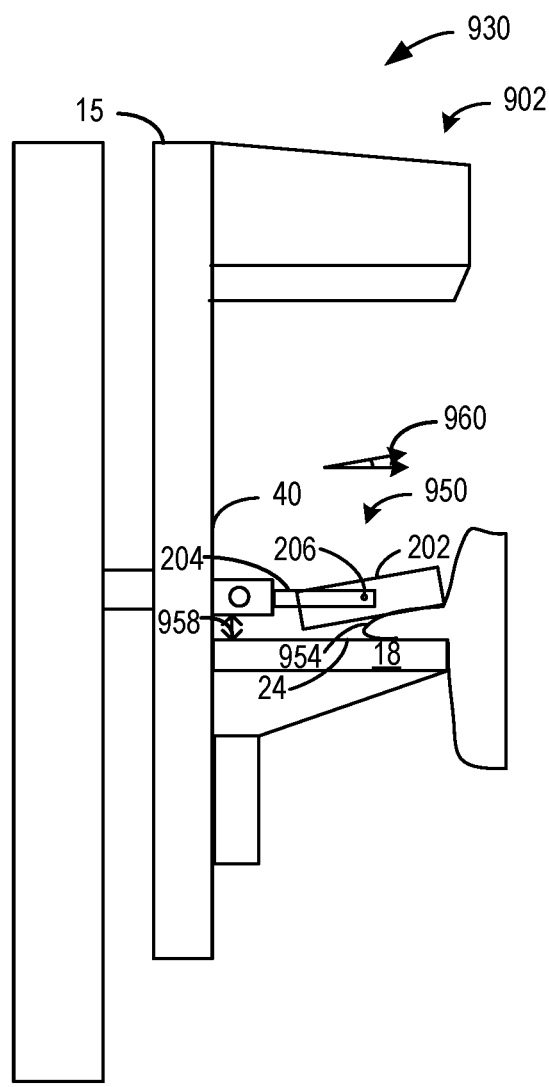
FIG. 9C shows the mammography system of FIG. 1, including a flexible paddle, in a compressed condition.

An exemplary embodiment of an x-ray system is shown in FIG. 1, which includes a compression arm assembly to which a flexible paddle may be removably coupled. When the imaging system is in a compressed condition, a paddle plate of the flexible paddle is at least partially in contact with the breast and a plurality of compliant mechanisms of the flexible paddle are elastically deformed, enabling the paddle plate to tilt, relative to a paddle frame of the flexible paddle, which is substantially horizontal. A first embodiment of the flexible paddle is shown in FIG. 2, and a second embodiment of the flexible paddle is shown in FIG. 4. FIG. 3 shows an embodiment of the paddle plate which may be included in at least one of the first embodiment and/or the second embodiment of the flexible paddle. The paddle plate has a projection extending perpendicularly from each of a first side and a second side of the paddle plate and into a respective cutout on a first arm and a second arm of the paddle frame. Each projection is coupled to the paddle frame by a plurality of compliant mechanisms to form a compliant, non-sliding, rotationally-flexible hinge. FIG. 5A shows a first embodiment of the hinge, FIG. 5B shows a second embodiment of the hinge, and FIG. 5C shows a third embodiment of the hinge. Elastic deformation of the hinge (e.g. having any one of the first, second, and third embodiments) enables tilting of the paddle plate relative to the paddle frame. FIGS. 6A, 6B, and 6C, respectively show the first embodiment of the hinge, the second embodiment of the hinge, and the third embodiment of the hinge in a non-elastically deformed configuration and in an elastically deformed configuration. FIG. 7 shows the flexible paddle in a first, untilted position, where both the paddle frame and the paddle plate are substantially horizontal. FIG. 8 shows the flexible paddle in a second, tilted position, where the paddle frame is substantially horizontal and the paddle plate is tilted to a first degree, relative to the paddle frame. FIGS. 9A, 9B, and 9C show an embodiment of the x-ray system, with the flexible paddle coupled thereto, in each of a procedure-ready condition, a compression-ready condition, and a compressed condition, respectively. A controller of the x-ray system may be configured to adjust the x-ray system among the procedure-ready condition, the compression-ready condition, and the compressed condition, as illustrated in a high-level flow chart of FIG. 10.

FIG. 1 shows a perspective view of an exemplary imaging system 100. The exemplary imaging system 100 may be a mammography system which includes an x-ray system 10 for performing a mammography procedure. The x-ray system 10 may be a tomosynthesis system, such as a digital breast tomosynthesis (DBT) system. The x-ray system 10 may be used to perform one or more procedures including digital tomosynthesis imaging, and DBT guided breast biopsy. Further, the x-ray system 10 may be utilized to perform a mammography imaging procedure, wherein one or more views including a craniocaudal (CC view) and a mediolateral oblique (MLO view) of a breast are obtained. The x-ray system 10 may be further used to perform other x-ray screening and diagnostic imaging procedures, including contract enhanced spectral mammography (CESM), and contrast enhanced DBT (CE-DBT) diagnostic imaging, and interventional procedures, including CESM-guided biopsy and stereotactic procedures.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation 62 of the gantry 15 housing the radiation source 16 indicates a rotation up to a desired degree on either direction about a vertical axis perpendicular to a horizontal detection surface of the radiation detector 18. For example, the angular range of rotation of the radiation source 16 may be −θ to +θ, where θ may be such that the angular range is a limited angle range, less than 360 degrees. An exemplary x-ray system may have an angular range of ±11 degrees, which may allow rotation of the gantry (that is rotation of the radiation source) from −11 degrees to +11 degrees about an axis of rotation of the gantry. The angular range may vary depending on the manufacturing specifications. For example, the angular range for DBT systems may be approximately ±11 degrees to ±60 degrees, depending on the manufacturing specifications.

The radiation source 16 is directed toward a volume or object to be imaged, the object positioned on a support platform 24 of the radiation detector 18, and is configured to emit radiation rays at desired times and to acquire one or more images. The radiation detector 18 is configured to receive the radiation rays. The detector 18 may be any one of a variety of different detectors, such as an x-ray detector, digital radiography detector, or flat panel detector. The collimator 20 is disposed adjacent to the radiation source 16 and is configured to adjust an irradiated zone of an object imaged. In some exemplary embodiments, the x-ray system 10 may further include a patient shield 36 mounted to the radiation source 16 such that a patient's body part (e.g., head) is not directly under the radiation.

The x-ray system 10 may further include a compression arm assembly 40, which may be movable upward and downward in relation to the gantry 15 along a vertical axis 60. Thus, the compression arm assembly 40 may be adjusted to be positioned closer to the radiation detector 18 by moving the compression arm assembly 40 downward toward the detector 18. The compression arm assembly 40 may include a flexible paddle 46, which may compress a body part, such as a breast, against the support platform 24 of the radiation detector 18. The flexible paddle 46 may be removably coupled to the compression arm assembly 40. A distance between the detector 18 and the flexible paddle 46 may be increased by moving the compression arm assembly 40 upward along the vertical axis 60 away from the detector 18, and a distance between the flexible paddle 46 and the detector 18 may be decreased by moving the compression arm assembly 40 downward along the vertical axis 60 towards the detector 18. As further described with respect to FIGS. 2-6C, the flexible paddle 46 comprises a compliant, non-sliding, rotationally-flexible hinge comprising a paddle plate coupled to a paddle frame by a plurality of compliant mechanisms with elastic deformation. The paddle plate may tilt, with respect to the paddle frame, when the paddle plate is at least partially in contact with the body part. The paddle frame is remains substantially horizontal. In this way, the flexible paddle 46 may be utilized to compress the body part to minimize the thickness traversed by the x-rays and to help reduce movement of the body part due to the patient moving.

The imaging system 100 may further include workstation 43 comprising a controller 44 including at least one processor and a memory. The controller 44 may be communicatively coupled to one or more components of the x-ray system 10 including one or more of the radiation source 16 and the radiation detector 18. In one exemplary embodiment, the communication between the controller and the x-ray system 10 may be via a wireless communication system. In other exemplary embodiments, the controller 44 may be in electrical communication with the one or more components of the x-ray system via a cable 47. Further, in an exemplary embodiment, as shown in FIG. 1, the controller 44 is integrated into workstation 43. In other exemplary embodiments, the controller 44 may be integrated into one or more of the various components of the system 10 disclosed above. Further, the controller 44 may include processing circuitry that executes stored program logic and may be any one of a plurality of different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 56, a keyboard 52, mouse 54, and/or other appropriate user input devices that facilitate control of the system 10 via a user interface 50.

Through its processors and controllers, the controller 44 may adjust the operation and function of the x-ray system 10. As an example, the controller 44 may provide timing control, as to when the radiation source 16 emits x-rays, and may further adjust how the detector 18 reads and conveys information or signals after the x-rays hit the detector 18, and how the radiation source 16, the detector 18, and the compression arm assembly 40, including the flexible paddle 46, move relative to one another and relative to the body part. The controller 44 may also control how information, including images and data acquired during the operation, is processed, displayed, stored, and manipulated. The different processing steps, including receiving one or more signals from one or more sensors, receiving user input, evaluating the received signals/input, image processing, determining reconstruction error, outputting operation parameters including error indications, adjusting one or more actuators of the x-ray system to control operation of the x-ray system, performed by the controller 44, may be provided by a set of instructions stored in non-transitory memory of the processor. Information may also be stored in one or more non-transitory memories of controller 44 for later retrieval and use.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the flexible paddle 46. Thus, a volume of the x-ray system 10 between the flexible paddle 46 and the detector 18 is an imaging volume. The radiation source 16 then emits radiation rays on to the compressed breast, and a projection image of the breast is formed on the detector 18. The projection image may then be reconstructed by the controller 44, and displayed via the display portion 50 on the interface 56.

FIG. 2 illustrates a first embodiment of a flexible paddle 200 which may be used as a compression paddle for a mammography device, such as the flexible paddle 46 of the imaging system 100 of FIG. 1. The flexible paddle 200 shown in FIG. 2 comprises a paddle frame 204 and a paddle plate 202. The paddle plate 202 is coupled to the paddle frame 204 by a plurality of compliant mechanisms to form a compliant, non-sliding, rotationally-flexible hinge, herein "hinge", at a position indicated by a circle 206 and as further described with respect to FIGS. 4-6C. The hinge enables the paddle plate 202 to hinge (e.g., tilt) with respect to the paddle frame 204, and defines an axis of rotation of the paddle plate 202 relative to the paddle frame 204. For example, the paddle plate 202 may hinge about an axis of rotation 208 in a direction indicated by an arrow 210, and the paddle frame 204 may remain substantially horizontal when coupled to a mammography device.

The paddle frame 204 comprises a first arm 212, a second arm 214 parallel to and spaced apart from the first arm 212, and a cross bar 216 which is perpendicular to, continuous with, and couples the first arm 212 and the second arm 214. Each of the first arm 212, the second arm 214, and the cross bar 216 have a first height 218, which may be less than a second height 238 of the paddle plate 202, as further described herein. The hinge, indicated by the circle 206, is positioned at a first end 220 of each of the first arm 212 and the second arm 214. Further detail regarding configuration and operation of the hinge is described with respect to FIGS. 5A-6C. The cross bar 216 couples the first arm 212 and the second arm 214 at a second end 230 of the first arm 212 and the second arm 214, opposite the first end 220. In some embodiments of the flexible paddle, such as the example shown in FIG. 2, the cross bar 216 further comprises a coupling extension 236 which extends in a direction opposite the first arm 212 and the second arm 214 (e.g., away from the first end 220 and the second end 230). The coupling extension 236 may have a shape which is complementary to a compression arm assembly, for example, the compression arm assembly 40 of FIG. 1, such that the flexible paddle 200 may be removably coupled to the compression arm assembly 40 via the coupling extension 236 of the paddle frame 204. The flexible paddle 200 may be removably coupled to the compression arm assembly 40 by a slide-in, clip-in, and/or other coupling method. Removably coupling the flexible paddle 200 to the compression arm assembly 40 may allow for removal and cleaning and/or replacement of the flexible paddle 200 between scans and/or between patients.

The paddle plate 202 may have a bowl shape, comprising a base 232, a first wall 228, a second wall 226 opposite the first wall 228, a first side 222 perpendicular to and coupling the first wall 228 and the second wall 226, and a second side 224 opposite the first side 222, the second side 224 perpendicular to and coupling the first wall 228 and the second wall 226. Intersections among walls, sides, and the base of the paddle plate 202 may be curved, compared to linear, angled intersections, in some examples.

The paddle plate 202 is coupled to the paddle frame 204 at the hinge, indicated by the circle 206, which is positioned at an approximate mid-region 234 of the paddle plate 202. Positioning of the hinge at the approximate mid-region of the paddle plate may be a conventional position for a hinge mechanism in other compression paddles. By positioning the hinge of the flexible paddle described herein at a conventional hinge position, the flexible paddle 200 may be used with (e.g., removably coupled to) mammography systems without making adjustments to the mammography system.

An axis system 290 is provided in FIG. 2 for reference. The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples. The paddle plate 202 is enabled to tilt relative to the paddle frame 204 by the hinge, and the paddle plate 202 remains substantially in one position within a plane. For example, the paddle plate 202 is anchored to the paddle frame 204 along the axis of rotation 208 by projections of the paddle plate 202 coupled to cutouts of the paddle frame 204 via a plurality of compliant mechanisms, as further described herein with respect to FIGS. 3-5C. Thus, the paddle plate 202 may not slide along the axis of rotation 208 (e.g., move along the x-axis, with respect to the axis system 290). When resistive force is applied to the base 232 of the paddle plate 202 in an upward direction along the y-axis, with respect to the axis system 290, the paddle plate 202 may tilt such that the first wall 228 moves upwards with respect to the y-axis and the second wall 226 moves downwards with respect to the y-axis. Along the axis of rotation 208, the paddle plate 202 is stationary (e.g., does not move up or down with respect to the y-axis). Further detail regarding tilting of the paddle plate 202 relative to the paddle frame 204 is described with respect to FIGS. 6A-9C.

In some examples, the paddle frame 204 and the paddle plate 202 may be formed using injection molding or additive manufacturing methods such as 3D printing. For example, the paddle frame 204 may be overmolded onto the paddle plate 202. The overmolded design of the flexible paddle 200 may reduce a weight and number of parts of the flexible paddle, compared to conventional compression paddles which use a series of elastomers, springs and/or other elements formed of materials such as metal. The flexible paddle described herein may be formed using a single injection mold. In this way, a flexible mechanism (e.g., the hinge having the plurality of compliant mechanisms) may be formed without assembly of multiple parts. The flexible paddle 200 may be a single, heterogeneous part, where the paddle plate 202 and the paddle frame 204 are coupled at the flexible mechanism (e.g., the hinge), which also serves as a pivot point for the paddle plate 202, as further described herein. The paddle frame 204, may be formed of a first material, such as plastic or nylon. The paddle plate 202 may be formed of a second material, different from the first material, such as plastic or other lightweight, durable, inexpensive material such as nylon, Lexan, and so on. For example, forming the flexible paddle 200 of plastic and/or other lightweight material which may be molded to the desired shape of the flexible paddle 200 may result in a flexible paddle 200 which is 30% lighter, compared to a conventional paddle which is at least partially formed of metal. The paddle plate 202 may be formed of at least partially transparent material in some examples. In the example of FIG. 2, the paddle plate 202 is formed of at least partially transparent material, thus at least a portion of a structure of the paddle frame 204 may be visualized through the paddle plate 202 (e.g., as indicated by regions having striped infill). In other examples, the paddle plate 202 may be formed of non-transparent material. By forming the paddle plate 202 of at least partially transparent material, positioning of the breast may be made at least partially less challenging, for example, allowing an operator to visualize a position of the breast and more easily determine whether to adjust the breast position, compared to paddle plates formed of non-transparent material.

Turning to FIG. 3, an example paddle plate 300 is shown. The paddle plate 300 may be an example of the paddle plate 202 of FIG. 2, and elements of the paddle plate which are introduced with respect to FIG. 2 are equivalently numbered in FIG. 3 and some may not be reintroduced, for brevity. The paddle plate 300 is formed as a substantially square dish having a patient end 320 and a device end 330, opposite the patient end 320. The first wall 228 extends along the patient end 320, the second wall 226 extends along the device end 330. When coupled to the paddle frame 204, as shown in FIG. 2, the first side 222 and the second side 224 are parallel with and adjacent to the first arm 212 and the second arm 214, respectively, of the paddle frame 204. The base 232 of the paddle plate 300, which acts as a compression surface and may be at least partially in contact with a breast when the flexible paddle is coupled to a mammography device, is substantially planar. In the example shown in FIG. 3, the second wall 226, the first side 222, and the second side 224 flare outward from the base 232 (e.g., away from the central axis 302). In other examples, such as the flexible paddle of FIG. 4, the first wall 228, the second wall 226, the first side 222, and the second side 224 may extend substantially perpendicular to the base 232.

The paddle plate 300 may have a sloped extension 326 which extends from the second wall 226 in a direction away from a central axis 302 of the paddle plate 300. In some embodiments, the sloped extension 326 of the paddle plate 300 may be at least partially covered by the coupling extension 236 of the paddle frame 204, for example, as shown in FIG. 2. The sloped extension 326 of the paddle plate 300 may be used in addition to or instead of the coupling extension 236 of the paddle frame 204 to removably couple the flexible paddle 200 to a mammography device (e.g., to the compression arm assembly 40 of the x-ray system 10).

As described above, the paddle plate 300 is coupled to the paddle frame 204 at the hinge. As further described herein, in some embodiments, the hinge is formed of a projection 304 which extends from the paddle plate 300 and is coupled to the paddle frame 204 via a plurality of compliant mechanisms. For example, the projection 304 is positioned on each of the first side 222 and the second side 224 of the paddle plate 300 at the approximate mid-region 234. The projection 304 extends perpendicular to each of the first side 222 and the second side 224 of the paddle plate 300, away from the central axis 302 of the paddle plate 300. In the example shown in FIG. 3, the projection 304 has a cylindrical shape with a first face 306 (e.g., a circular face) and a body 308 (e.g., a cylindrical body). The first face 306 is substantially perpendicular to the base 232 of the paddle plate 300. The projection 304 extends substantially horizontal from the first side 222 and the second side 224, with the body 308 parallel to the base 232. When the first wall 228, the second wall 226, the first side 222, and the second side 224 are substantially perpendicular to the base 232, such as described with respect to FIG. 4, the first face 306 of the projection 304 may be in planar alignment with (e.g., parallel to) the first arm 212 and the second arm 214 of the paddle frame and parallel to the first side 222 and the second side 224. In other examples, the projection 304 may have another shape, such as a hexagonal face for the first face 306, and the body 308 having six planar faces coupling each edge of the hexagonal face to the respective side of the paddle plate 300. As further described with respect to FIGS. 5A-6C, a plurality of compliant mechanisms may extend radially from the body 308 of the projection 304 to couple the paddle plate 300 to the paddle frame 204.

Turning to FIG. 4, a second embodiment of a flexible paddle 400 is shown, which includes elements of the first embodiment of the flexible paddle 200. The flexible paddle 400 is a second embodiment of the flexible paddle 46 of the imaging system 100 of FIG. 1. Elements of the first embodiment which are included in the flexible paddle 400 are equally numbered and may not be reintroduced, for brevity. It is to be understood that the following description may be applied to the first embodiment of the flexible paddle 200, without departing from the scope of the present disclosure. The paddle plate 202 of the flexible paddle 400 as shown is not formed of transparent material, however the paddle plate 202 may be formed of at least partially or fully transparent material, in some examples.

The paddle frame 204 is configured with a cutout 402 on each of the first arm 212 and the second arm 214, adjacent to the first end 220 of the respective arm and in alignment with the approximate mid-region 234 of the paddle plate 202. The cutout 402 may be positioned such that a solid portion (e.g., not having a cutout) of the respective arm of the paddle frame 204 extends towards the first end 220 and the second end 230 of the respect arm on either side of the cutout 402. The cutout 402 may have a first diameter 412, which is less than a height 414 of each of the first arm 212 and the second arm 214. The cutout 402 extends at least partially into a width 404, perpendicular to a length 406, of each of the first arm 212 and the second arm 214. In the example shown in FIG. 4, the cutout 402 is circular and extends through the entire width 404, such that the cutout 402 is open to air and is unobstructed by the paddle frame 204 on either side of the width 404 of the respective arm, parallel to the respective side of the paddle plate 202 (e.g., the first side 222 or the second side 224). In other examples, the cutout 402 may extend partially through the width 404, where an opening of the cutout 402 adjacent to the paddle plate 202 is unobstructed by the paddle frame 204 and a side of the cutout 402 parallel to and distal from the paddle plate 202 is obstructed (e.g., covered) by material of the paddle frame 204. An example of a cutout which partially extends into the width of the paddle frame 204 is shown in the first embodiment of the paddle frame 204 of FIG. 2, where the cutout is not visible in the first arm 212 or the second arm 214.

The second embodiment of the flexible paddle 400 of FIG. 4 includes a hinge 408 where each of a plurality of compliant mechanisms couple the projection of the paddle plate 202 to the paddle frame 204. A conventional hinge may include a pintle, such as a pin or a bolt, inserted into a socket-like, cylindrical gudgeon, where a first component attached to the pintle may pivot or hinge with respect to a second component coupled to the gudgeon. In the hinge 408 described herein, the projection of the paddle plate 202 acts as a pintle which is inserted into a cutout (e.g., a gudgeon) of the paddle frame 204, enabling the paddle plate 202 to pivot relative to the paddle frame 204. Additionally, the hinge 408 includes the plurality of compliant mechanisms (e.g., as shown in FIGS. 5A-5C) which are engaged with and couple the projection to the cutout. Each of the plurality of compliant mechanisms may function as a type of living hinge, where each compliant mechanism is continuous with (e.g., formed of the same material as) the projection and the cutout. As further described herein, each compliant mechanism may be configured to elastically deform in one or more planes may be elastic, such that the compliant mechanism may contract to a contracted configuration and relax back to a relaxed configuration multiple times.

The projection (e.g., the projection 304, shown in FIG. 3) of the paddle plate 202 extends into the cutout 402 of the paddle frame 204 and is coupled to the paddle frame 204 by the plurality of compliant mechanisms. For example, a first end of a compliant mechanism of the plurality of compliant mechanisms is coupled to the projection, and a second end, opposite the first end, of the compliant mechanism is coupled to an inner wall 410 of the cutout 402, as further described with respect to FIGS. 5A-5C. In some examples, a length of the projection (e.g., parallel to the width 404) may be less than the width 404 of the respective first arm 212 or second arm 214, and is therefore less than a width of the cutout 402 (e.g., parallel to the width 404). In this way, when the cutout 402 is closed at the side parallel to and distal from the paddle plate 202 (e.g., obstructed by the paddle frame 204), the first face 306 of the projection 304 may not be in contact with the paddle frame 204. In other examples, as described with respect to FIGS. 5A-5C, a length of the projection may be equal to the width of the cutout 402, such that the first face 306 of the projection 304 is in the same plane as a face 416 of the respective arm. A width of the projection 304 (e.g., a diameter of the first face 306 of the projection 304) may be less than the first diameter 412 of the cutout 402. This may allow the projection 304 to rotate with elastic deformation of the plurality of compliant mechanisms which are coupled to the projection 304 (e.g., as further described with respect to FIGS. 5A-6C), enabling the paddle plate 202 to tilt relative to the paddle frame 204.

Example embodiments of the hinge 408 are herein described with respect to FIGS. 5A, 5B, and 5C. As described above, the hinge 408 may be configured as a projection (e.g., of the paddle plate) extending into and coupled to a cutout (e.g., of the paddle frame) by a plurality of compliant mechanisms to form a compliant, non-sliding, rotationally-flexible hinge. A general configuration of the hinge 408 is first described with respect to FIG. 5A, and is applicable to the embodiments described with respect to FIGS. 5B and 5C. An axis system 590 is provided in FIGS. 5A-5C for reference. The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples.

Each of a plurality of compliant mechanisms 516 extend radially from the body 308 of the projection 304, the body 308 extending parallel to the width 404 of the first arm 214 and the second arm 216 of the paddle frame 204. The plurality of compliant mechanisms may be equally distributed about the body 308 of the projection 304. In some examples, the plurality of compliant mechanisms 516 are continuous with and formed of the same material as the projection 304 and the paddle plate 202. In another example, the plurality of compliant mechanisms 516 are continuous with and formed of the same material as the paddle frame 204. In further examples, the plurality of compliant mechanisms 516 may be continuous with and formed of the same material as both of or neither of the paddle plate 202 and the paddle frame 204. In some examples, some of the plurality of compliant mechanisms 516 (e.g., alternating compliant mechanisms, moving clockwise around the projection 304) are formed of the same material and coupled to the paddle frame 204, and other compliant mechanisms are formed of the same material and coupled to the paddle plate 202.

The plurality of compliant mechanisms 516 which couple the projection 304 to the paddle frame 204 form a compliant, non-sliding, rotationally-flexible hinge (e.g., hinge) that achieves force and motion transmission through elastic body deformation. The hinge gains some or all of its motion from the relative flexibility of the plurality of compliant mechanisms rather than from rigid-body joints alone. Flexible motion (e.g., rotational compression and relaxation) of the plurality of compliant mechanisms is enabled by material properties of the plurality of compliant mechanisms (e.g., plastic flexibility), as well as the shape provided at the hinge point, as further described with respect to FIGS. 5A-8. Although the plurality of compliant mechanisms of the hinge are configured to elastically deform, the hinge itself is a compliant, non-sliding hinge, meaning that during elastic deformation of the plurality of compliant mechanisms, the projection 304 and paddle frame 204 remain substantially in one position. For example, neither the projection 304 nor the paddle frame 204 move along the z-axis or the x-axis, with respect to the axis system 590. Instead, the plurality of compliant mechanisms elastically deform about the central axis of rotation, which is parallel with the z-axis and extends through a center of the projection 304. For example, the plurality of compliant mechanisms rotationally flex about a center point of the projection 304, contracting and/or expanding in a clockwise and/or counterclockwise direction, depending on whether the paddle plate 202 is moving from a substantially horizontal position to a tilted position, with respect to the paddle frame 204, as further described herein. The paddle plate 202 may pivot relative to the paddle frame 204 without moving along an axis perpendicular to the axis of rotation and without moving along the axis of rotation, as further described with respect to FIGS. 7-8.

In a first example hinge 510 shown in FIG. 5A, each of the plurality of compliant mechanisms 516 is a curved extension configured to act as a linear spring in a first plane and a second plane, perpendicular to the first plane. Each compliant mechanism is curved such that a first end 522 of a compliant mechanism is coupled to the body 308 of the projection 304 and is radially aligned with a first position 524 on the cutout 402, and a second end 526 of the compliant mechanism is coupled to the inner wall 410 of the cutout 402 and is radially aligned with a second position 528 on the cutout 402, the second position 528 different from the first position 524. The cutout 402 has a cylindrical shape which extends through the width 404 of the respective arm (e.g., the first arm 212) of the paddle frame 204. In the first example hinge 510, the projection 304 has a cylindrical shape. The plurality of compliant mechanisms extend radially from the projection 304 and curve in a counterclockwise direction. In some examples (e.g., as shown in FIG. 6A), the plurality of compliant mechanisms may curve in a clockwise direction. For example, a first end of a first compliant mechanism 502 is coupled to and/or continuous with the projection 304, and extends and curves away from the projection 304 to couple to the inner wall 410 of the cutout 402 at a second end of the first compliant mechanism 502, opposite the first end.

In some examples of the first example hinge 510, alternating compliant mechanisms of the plurality of compliant mechanisms 516 are staggered along a length of the body 308 of the projection 304. A second view 515 shows a section of the first example hinge 510 taken along the dashed line A, bisecting the projection 304. The second view 515 shows the first compliant mechanism 502 expanding a width of the projection 304, the width of the projection 304 equal to the width 404 of the respective arm in the example of FIG. 5A. A body of the first compliant mechanism 502 extends along the length of the body 308 of the projection 304 (e.g., along the z-axis). A second compliant mechanism 504, adjacent to the first compliant mechanism 502, may be set back along the length of the body 308 a non-zero distance from the first face 306 of the projection 304 (e.g., along the z-axis). The remaining compliant mechanisms of the plurality of compliant mechanisms may alternate in their positioning with respect to alignment with the first face 306 of the projection. For example, a body of a third compliant mechanism 506 extends along the length of the body 308 of the projection 304. A fourth compliant mechanism 508 is set back a distance 512 from the first face 306 of the projection 304. The second compliant mechanism 504 and the fourth compliant mechanism 508 are thus in a second plane, different from the first plane of the first face 306, the first compliant mechanism 502, and the third compliant mechanism 506. Additionally, at least some of the plurality of compliant mechanisms 516 which extend the length of the body 308 of the projection 304 may extend into a second plane from a first plane, enabling the compliant mechanism to operate as a linear spring in two planes. For example, the first compliant mechanism 502 which is coupled to the projection 304 in the same plane as the first face 306 of the projection 304 may extend along the length of the body 308.

The plurality of compliant mechanisms are configured to be elastically deformable in two planes. For example, each of the plurality of compliant mechanisms may act as a linear spring in two planes, where each compliant mechanism deforms to a contracted configuration in a first condition, and returns (e.g., "springs" or "elastics" back) to a relaxed configuration in a second condition. By configuring the plurality of compliant mechanisms to be deformable in two planes (e.g., operate as linear springs in two planes), a durability of the hinge may be increased, relative to compliant mechanisms configured to be deformable in one plane (e.g., operate as linear springs in one plane), such that a time and a force applied to degrade the plurality of compliant mechanisms to operate as linear springs in two planes is greater than a time and a force applied to degrade a plurality of compliant mechanisms configured to operate as linear springs in one plane. Additionally, the configuration of the plurality of compliant mechanisms as linear springs in two planes may provide increased stability, retention, and smoother movement (e.g., tilt of the paddle plate), compared to other compliant mechanism configurations. For example, when a compliant mechanism is configured to act as a linear spring in only one plane, the compliant mechanism may be susceptible to forces applied in the other two planes, which may result in undesirable deformation (e.g., deformation in a direction other than the intended direction) of the compliant mechanism. Compliant mechanisms which are configured to elastically deform in two or more planes may be able to withstand forces applied along multiple planes and thus be more resistant to undesirable deformation than compliant mechanisms configured to elastically deform in only one plane.

In a second example hinge 520, shown in FIG. 5B, each of the plurality of compliant mechanisms is a curved extension between the projection 304 and the cutout 402 of the paddle frame (e.g., the first arm 212 and/or the second arm 214 of the paddle frame). The plurality of compliant mechanisms are configured to be elastically deformable in one plane. For example, the plurality of compliant mechanisms may act as linear springs in one plane, where each compliant mechanism deforms to a contracted configuration in a first condition, and returns (e.g., "springs" or "elastics" back) to a relaxed configuration in a second condition. The projection 304 extends from the paddle plate 202 as described with respect to the first example hinge 510 and FIG. 3. The cutout 402 of the paddle frame 204 is substantially circular with angled extensions 538 and a receiving body 540. The receiving body 540 is suspended in the cutout 402 by the plurality of compliant mechanisms 516, where the angled extensions 538 are each coupled to a compliant mechanism of the plurality of compliant mechanisms. The receiving body 540 is configured to have the projection 304 of the paddle plate positioned therein and coupled thereto, for example, by snap fitting, press fitting, molding, or other coupling method. In this way, the receiving body 540 functions as an extension of the projection 304 and rotates with rotation of the projection 304, which results in elastic deformation of the plurality of compliant mechanisms, as described herein.

In the example shown in FIG. 5B, the plurality of compliant mechanisms are comprised of a first compliant mechanism 532, a second compliant mechanism 534, and a third compliant mechanism 536, which are continuous with and equally distributed about the receiving body 540. In other examples, the plurality of compliant mechanisms may include more than or less than three compliant mechanisms. In the second example hinge 520, the projection 304 has a hexagonal shape which fits into a hexagonal opening at the center of the receiving body 540. The receiving body 540 may have a different shaped opening into which a different shaped projection 304 may fit, without departing from the scope of the present disclosure.

Each of the plurality of compliant mechanisms may be configured such that a front face of compliant mechanism (e.g., a front face 542 of the first compliant mechanism 532)

is continuous with and in the same plane as a front face 544 of the receiving body 540. A back face of the compliant mechanism is parallel with the front face and spaced apart by a width of the compliant mechanism, (e.g., the width extending into the width of the respective arm of the paddle plate, along the z-axis). The back face of the compliant mechanism may be continuous with and in the same plane as a back face of the receiving body 540 (e.g., parallel with and spaced apart from the front face 544 of the receiving body 540 by a width of the receiving body 540, along the z-axis). With respect to the axis system 590, the configuration of the plurality of compliant mechanisms described with respect to FIG. 5B are configured to elastically deform (e.g., expand and relax) in the YX-plane. Each of the plurality of compliant mechanisms couple the receiving body 540, and thus the projection 304, to the arm of the paddle frame 204 (e.g., the first arm 212 or the second arm 214). As further described with respect to FIGS. 6B and 7-9B, the plurality of compliant mechanisms may be elastically deformed when force is exerted on the paddle plate 202, enabling which includes rotational compression of each of the plurality of compliant mechanism, and may result in rotation of the projection 304 and tilting of the paddle plate 202.

In a third example hinge 530, shown in FIG. 5C, each of the plurality of compliant mechanisms is a linear notched extension between the projection and the cutout of the paddle frame, and the plurality of compliant mechanisms are configured to contract and expand in one plane. The projection 304 extends from the paddle plate 202 as described with respect to the first example hinge 510 and the second example hinge 520. The cutout 402 of the paddle frame 204 is substantially circular with a receiving body 540 suspended therein by the plurality of compliant mechanisms 516, where the receiving body 540 is coupled to the cutout 402 by the plurality of compliant mechanisms. The receiving body 540 is configured to have the projection 304 of the paddle plate positioned therein and coupled thereto, for example, by snap fitting, press fitting, molding, or other coupling method. In the third example hinge 530, the projection 304 has a hexagonal shape which fits into a hexagonal opening at the center of the receiving body 540. The receiving body 540 may have a different shaped opening into which a different shaped projection 304 may fit, without departing from the scope of the present disclosure. In this way, the receiving body 540 functions as an extension of the projection 304 and rotates with rotation of the projection 304, which results in elastic deformation of the plurality of compliant mechanisms, as described herein.

In the example shown in FIG. 5C, the plurality of compliant mechanisms are comprised of a first compliant mechanism 552, a second compliant mechanism 554, and a third compliant mechanism 556. In other examples, the plurality of compliant mechanisms may include more than or less than three compliant mechanisms. Each of the plurality of compliant mechanisms may be configured such that a front face of compliant mechanism (e.g., a front face 562 of the first compliant mechanism 552) is continuous with and in the same plane as the front face 544 of the receiving body 540. A back face of the compliant mechanism is parallel with the front face and spaced apart by a width of the compliant mechanism, (e.g., along the z-axis). The back face of the compliant mechanism may be continuous with and in the same plane as a back face of the receiving body 540 (e.g., parallel with and spaced apart from the front face 544 of the receiving body 540 by a width of the receiving body 540, along the z-axis).

With respect to the axis system 590 the configuration of the plurality of compliant mechanisms described with respect to FIG. 5C are configured to elastically deform (e.g., expand and relax) in the YX-plane. Each of the plurality of compliant mechanisms couple the receiving body 540, and thus the projection 304, to the arm of the paddle frame 204 (e.g., the first arm 212 or the second arm 214). Each compliant mechanism of the plurality of compliant mechanisms includes at least one notch positioned along a first edge 570 of the compliant mechanism. The at least one notch may extend partially towards a second edge 572, opposite the first edge 570. The at least one notch further extends along a length of the respective compliant mechanism (e.g., parallel to the width 404 of the respective arm of the paddle frame 204. Each of the at least one notch may be a valley in the compliant mechanism and have a V, U, C, or other concave shape, for example. For example, a single notch on a compliant mechanism may form a peak adjacent to the cutout 402, a peak adjacent to the projection 304 (e.g., the receiving body 540 into which the projection 304 is inserted), and a valley therebetween, along the first edge 570. During rotation of the projection 304 and deformation of the compliant mechanisms, the single notch may fold such that there is no valley between the peaks, and the first edge 570 of each compliant mechanism is continuous, as further described with respect to FIG. 6C.

As shown in a detailed view 560, each of the linear notched extensions includes a first notch 564 and a second notch 566, each having a first face 574 and a second face 576. The first face 574 and the second face 576 may be spaced apart when the third example hinge 530 is not elastically deformed, as further described with respect to FIG. 6C. The first notch 564 and the second notch 566 together form three peaks and two valleys, with a peak on either side of each valley along the first edge 570. Each of the first notch 564 and the second notch 566 may be identical in shape and size for each of the plurality of compliant mechanisms. In other example, at least one of the first notch 564 and the second notch 566 may have a different size and/or shape for a compliant mechanism and/or among compliant mechanisms.

As further described with respect to FIGS. 6C-9C, the plurality of compliant mechanisms may be elastically deformed, which includes rotational compression of each of the plurality of compliant mechanism, and may result in rotation of the projection 304 and tilting of the paddle plate 202. For example, each of the plurality of compliant mechanisms has a first notch 564 and a second notch 566 along a first edge, each of the first notch 564 and the second notch 566 extending along a width of the compliant mechanism (e.g., along the z-axis). Elastic deformation of the plurality of compliant mechanisms described with respect to FIG. 5C includes rotation of the projection 304 in a first direction and compression of the plurality of compliant mechanisms such that the first notch 564 and the second notch 566 are folded to form a continuous edge along the first edge (e.g., without valleys where the notches are). Further detail regarding elastic deformation is described with respect to FIGS. 7-9C.

Turning to FIGS. 6A, 6B, and 6C, the first example hinge 510, the second example hinge 520, and the third example hinge 530 are shown, respectively, in a non-elastically deformed configuration (e.g., relaxed) and in an elastically deformed configuration (e.g., rotationally contracted). As described above, flexible motion (e.g., rotational contraction and relaxation) of the plurality of compliant mechanisms is enabled by material properties of the plurality of compliant mechanisms (e.g., plastic flexibility), as well as the shape provided at the hinge point. For example, each hinge may be in the non-elastically deformed configuration when the paddle plate is not in contact with the breast (e.g., a procedure-ready condition) and/or when the paddle plate is in contact with the breast but is not compressing the breast (e.g., a compression-ready condition), as is further described with respect to FIGS. 9A-10. When the hinge is in the non-elastically deformed configuration, the plurality of compliant mechanisms may be considered to be in a rotationally expanded configuration (e.g., are not rotationally contracted), and the paddle plate may be in a substantially horizontal position (e.g., parallel with the paddle frame). Generally, when the projection rotates in a first direction, a distance between a first end of a compliant mechanism and a second end of the compliant mechanism decreases. For the first example hinge 510 and the second example hinge 520, the first direction is the same as a direction of a curve of the compliant mechanism. For the third example hinge 530, the first direction is the same as a direction moving from a second edge of a compliant mechanism (e.g., the second edge having a continuous surface) to a first edge of the compliant mechanism (e.g., the first edge having at least one notch). The first end of each compliant mechanism may be an end adjacent and coupled to the projection and/or the receiving body coupled to the projection. The second end of each compliant mechanism may be an end adjacent and coupled to the inner wall of the cutout of the paddle frame.

An axis system 690 is provided in FIGS. 6A-6C for reference. The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples.

FIG. 6A shows a relaxed embodiment 600 and a rotationally contracted embodiment 610 of the first example hinge 510, described with respect to FIG. 5A. In the relaxed embodiment 600, each of the plurality of compliant mechanisms may be uncompressed (e.g., not elastically deformed). For example, there may be a first distance 604 between the projection 304 and a curve of a compliant mechanism (e.g., the first compliant mechanism 502, and so on). When a flexible paddle is coupled to an imaging system used for mammography, such as the x-ray system 10 of FIG. 1 and the method further described with respect to FIG. 10, the plurality of compliant mechanisms 516 may elastically deform (e.g., rotationally contract) in a first direction which is the same as the direction of paddle plate 202 tilt, indicated by a first curved arrow 606. Elastic deformation of the plurality of compliant mechanisms 516 results in the rotationally contracted embodiment 610 of the first example hinge 510.

In the rotationally contracted embodiment 610, there may be a second distance 608 between the projection 304 and the curve of a compliant mechanism, the second distance 608 different from the first distance 604. Additionally, as described with respect to FIG. 5A, the plurality of compliant mechanisms of the first example hinge 510 are configured to act as linear springs in two planes, enabling elastic deformation and flexibility of the plurality of compliant springs in a first plane (e.g., the YX-plane) and a second plane, perpendicular to the first plane (e.g., the YZ-plane). Rotating the projection 304 in the direction is also indicated by the first curved arrow 606. When the projection 304 rotates, a distance between the first end 522 and the second end 526 of each compliant mechanism decreases. The paddle plate 202 is thus rotated relative to the paddle frame 204, which is held within a fixed plane. In this way, the plurality of compliant mechanisms may enable tilting of the paddle plate 202 relative to the paddle frame 204, as further described with respect to FIGS. 7-10, while also providing additional stability, compared to compliant mechanisms which act as linear springs in one plane.

FIG. 6B shows a relaxed embodiment 620 and a rotationally contracted embodiment 630 of the second example hinge 520 having a plurality of compliant mechanisms configured to act as linear springs in one plane, described with respect to FIG. 5B. In the relaxed embodiment 620, each of the plurality of compliant mechanisms may be uncompressed (e.g., not elastically deformed). For example, there may be a first distance 612 between the receiving body 540 (e.g., into which the projection 304 may extend) and a curve of a compliant mechanism (e.g., the first compliant mechanism 532, the second compliant mechanism 534, and so on). When a flexible paddle is coupled to an imaging system used for mammography, such as the x-ray system 10 of FIG. 1 and the method further described with respect to FIG. 10, the plurality of compliant mechanisms may elastically deform (e.g., rotationally contract) in a first direction, which is the same as the direction of paddle plate 202 tilt, indicated by a second curved arrow 616. Elastic deformation of the plurality of compliant mechanisms results in the rotationally contracted embodiment 630 of the second example hinge 520. In the rotationally contracted embodiment 630, there may be a second distance 614 between the receiving body 540 and the curve of a compliant mechanism, the second distance 614 less than the first distance 612. In this way, the plurality of compliant mechanisms enable the paddle plate 202 to tilt relative to the paddle frame 204 while providing support in one plane (e.g., the YX-plane).

FIG. 6C shows a relaxed embodiment 640 and a rotationally contracted embodiment 650 of the third example hinge 530, described with respect to FIG. 5C. In the relaxed embodiment 640, each of the plurality of compliant mechanisms, configured as linear notched extensions, may be uncompressed (e.g., not elastically deformed). For example, each of the plurality of compliant mechanisms may extend linearly from the receiving body 540 (e.g., into which the projection 304 may extend) to the cutout 402. The first face 574 and the second face 576 may be spaced apart when the third example hinge 530 is in the relaxed embodiment 640. When a flexible paddle is coupled to an imaging system used for mammography, such as the imaging system 10 of FIG. 1 and the method further described with respect to FIG. 10, each of the linear notched extensions (e.g., the first compliant mechanism 552, the second compliant mechanism 554, and the third compliant mechanism 556) may elastically deform (e.g., rotationally contract) in a first direction, which is the same as the direction of paddle plate 202 tilt, indicated by a third curved arrow 626. Elastic deformation of the plurality of compliant mechanisms results in the rotationally contracted embodiment 650 of the third example hinge 530. In the rotationally contracted embodiment 650, each compliant mechanisms of the plurality of compliant mechanisms may be folded such that the first face 574 and the second face 576 of each of the notches (e.g., the first notch 564 and the second notch 566 of the first compliant mechanism 552) are in face sharing contact, and each compliant mechanism forms a continuous curve along the first edge 570 of the compliant mechanism. The second edge 572, opposite the first edge 570 of the first compliant mechanism 552, is the linear extension in the relaxed embodiment 640 and is curved in the rotationally contracted embodiment 650. All other compliant mechanisms of the third example hinge 530 (e.g., the second compliant mechanism 554 and the third compliant mechanism 556) may elastically deform in the same way as described with respect to the first compliant mechanism 552, where the first face 574 and the second face 576 of each notch are spaced apart in a relaxed embodiment and are in face sharing contact in a rotationally contracted embodiment. In some examples, each compliant mechanism of the third example hinge 530 may have more than or less than two notches, and in some examples, each compliant mechanism may have the same or a different number of notches. In this way, the paddle plate 202 may be enabled to tilt relative to the paddle frame 204 through elastic deformation of the plurality of compliant mechanisms.

FIGS. 5A-6C illustrate embodiments of hinges which may be used to couple a paddle plate to a paddle frame of a flexible paddle and enable tilting of the paddle plate relative to the paddle frame by elastic deformation of compliant mechanisms of each hinge. FIGS. 7 and 8 show example configurations of the flexible paddle in an untilted and in a tilted configuration, respectively. The flexible paddle shown in FIGS. 7 and 8 may be an example of the flexible paddle 200 of FIG. 2 and/or the flexible paddle 400 of FIG. 4, and includes the second example hinge 520 described with respect to FIGS. 5B and 6B. The flexible paddle 710 may include the first example hinge 510 and/or the third example hinge 530 instead of the second example hinge 520 to enable tilting as described with respect to the second example hinge 520 without departing from the scope of the present disclosure.

FIG. 7 shows the flexible paddle 710 in an untilted configuration 700. An axis system 790 is provided in FIG. 7 for reference. The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples. The flexible paddle 710 may be in the untilted configuration 700 when coupled to an imaging system (e.g., the imaging system 10 of FIG. 1) and in one of a procedure-ready condition and/or a compression-ready condition, as further described with respect to FIGS. 9A-10. In the untilted configuration 700, the paddle plate 202 is not tilted, relative to the paddle frame 204. Described another way, the base 232 of the paddle plate 202 is substantially horizontal and parallel to the paddle frame 204 (e.g., to a top face 704 of the first arm 212 and the second arm 214 of the paddle frame 204). For example, the paddle plate 202 (e.g., the base 232 of the paddle plate 202 and all surfaces parallel thereto) and the paddle frame 204 (e.g., the top face 704 of the first arm 212 and all surfaces parallel thereto) are parallel with the z-axis, with respect to the axis system 790. The second example hinge 520 is in a relaxed, non-elastically deformed configuration.

FIG. 8 shows the flexible paddle 710 in a tilted configuration 800. The axis system 790 is provided in FIG. 8 for reference and is configured as described with respect to FIG. 7. The flexible paddle 710 may be in the tilted configuration 800 when coupled to an imaging system (e.g., the imaging system 10 of FIG. 1) and in a compressed condition, as further described with respect to FIGS. 9A-10. In the compressed condition, the base 232 of the paddle plate 202 is at least partially in contact with a breast of a patient and is exerting a downward pressure onto the breast. As a result of resistance from the breast, the paddle plate 202 tilts, relative to the paddle frame 204, as enabled by elastic deformation of the plurality of compliant mechanisms of the hinge (e.g., the second example hinge 520). The base 232 of the paddle plate 202 is tilted to a first degree 802, relative to the paddle frame 204, which remains substantially horizontal. For example, the paddle frame 204 (e.g., the top face 704 of the first arm 212 and all surfaces parallel thereto) is parallel with the z-axis, with respect to the axis system 790, and the paddle plate 202 (e.g., the base 232 of the paddle plate 202 and all surfaces parallel thereto) are tilted to the first degree 802 from the z-axis. The first degree 802 may be 12.5 degrees, in some examples. The hinge is in a compressed, elastically deformed configuration, as described with respect to FIGS. 6A-6C. Specifically, the second example hinge 520 is in the rotationally contracted embodiment 630 of FIG. 6B. The hinge, the paddle plate 202, and the paddle frame 204 may be configured such that the paddle plate 202 may tilt through a range of angles, relative to the paddle frame 204. For example, the angle at which the paddle plate 202 may tilt may be greater than or less than 12.5 degrees, in some examples. The angle (e.g., the degree of tilt) may depend on downward pressure exerted by the paddle plate 202 onto the breast, resistance from the breast, and a size of the breast, for example.

Figure 10:
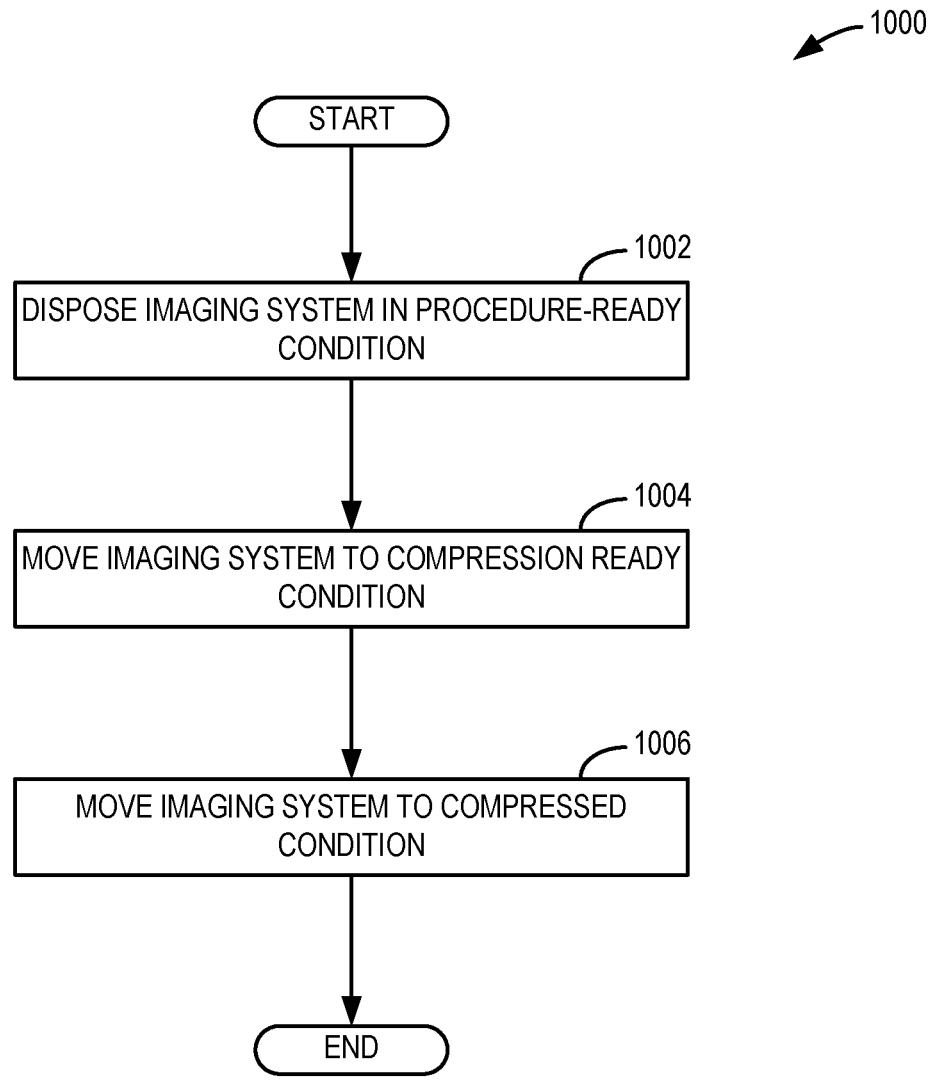
FIG. 10 shows a flow chart illustrating adjustment of the mammography system of FIGS. 9A-9C among the procedure-ready condition, the compression-ready condition, and the compressed condition.

FIGS. 9A, 9B, and 9C show an embodiment of an imaging system 902, with the flexible paddle coupled thereto, in each of a procedure-ready condition 900, a compression-ready condition 920, and a compressed condition 930. A controller of the imaging system 902 may be configured to adjust the imaging system among the procedure-ready condition, the compression-ready condition, and the compressed condition, as illustrated in a high-level flow chart of FIG. 10. For example, the imaging system 902 may be an example of the imaging system 10 of FIG. 1 communicably coupled to the workstation 43, and the controller of the imaging system may be an example of the controller 44. FIGS. 9A-10 are herein described simultaneously, where a method 1000 of FIG. 10 is used to adjust the imaging system to the positions shown in FIGS. 9A-9C.

At 1002, the method 1000 includes disposing the imaging system in a procedure-ready condition. As shown in FIG. 9A, when the imaging system 902 is in the procedure-ready condition 900, a flexible paddle 950 is coupled to a compression arm assembly 40 of the imaging system 902. The flexible paddle 950 may be an example of any of the flexible paddles 200, 400, and 710, and may be configured with any of the first example hinge 510, the second example hinge 520, and the third example hinge 530 at the approximate midpoint of the paddle plate 202 and the first end of the paddle frame 204, as indicated by the circle 206. The paddle plate 202 and the paddle frame 204 of the flexible paddle 950 are substantially horizontal (e.g., parallel to the support platform 24), and the compression arm assembly 40 is a first height 952 above the support platform 24. The compression arm assembly 40 is thus in a first linear position, proximate to the radiation detector 18. When the imaging system is in the procedure-ready condition 900, a patient breast 954 may be positioned on the support platform 24.

At 1004, the method 1000 includes moving the imaging system to a compression-ready condition. As shown in FIG. 9B, when the imaging system 902 is in the compression-ready condition 920, the paddle plate 202 and the paddle frame 204 are substantially horizontal, and the compression arm assembly 40 is disposed at a second height 956 above the support platform 24. The second height 956 is less than the first height 952 at which the compression arm assembly 40 is positioned in the procedure-ready condition 900. The paddle plate 202 is at least partially in contact with the patient breast 954, however the patient breast 954 is not substantially compressed.

At 1006, the method 1000 includes moving the imaging system to a compressed condition. During movement to the compressed condition 930, an elastic deformation of a plurality of compliant mechanisms which couple the paddle plate 202 to the paddle frame 204 is performed substantially simultaneously with a pivotal movement of the paddle plate 202 and a linear movement of the compression arm assembly 40. For example, the compression arm assembly 40 moves downward (e.g., towards the support platform 24) along a track of the gantry 15, and the paddle plate 202 tilts relative to the paddle frame 204 at the hinge, indicated by the circle 206. A force from the downward linear movement of the compression arm assembly 40, and the flexible paddle 950 coupled thereto, is exerted on the patient breast 954, which exerts an opposing force. The opposing force (e.g., resistance) of the patient breast 954 may be greater closer to the patient (e.g., the patient end of the flexible paddle 950, as described with respect to FIGS. 3 and 4) than the opposing force of the patient breast 954 closer to the gantry 15. Elastic deformation of the plurality of compliant mechanisms coupling the paddle plate 202 to the paddle frame 204 may enable the paddle plate 202 to tilt relative to the paddle frame 204.

As shown in FIG. 9C, when the imaging system 902 is in the compressed condition 930, the compression arm assembly 40 is disposed at a third height 958, the third height 958 less than the second height 956 at which the compression arm assembly 40 is positioned in the compression-ready condition 920. When at the third height 958, the compression arm assembly 40 is in a second linear position, proximate to the radiation detector 18. The paddle frame 204 is substantially horizontal. The paddle plate 202 is at least partially in contact with the patient breast 954 and a plurality of compliant mechanisms coupling the paddle plate 202 to the paddle frame 204 are elastically deformed, thus tilting the paddle plate 202 to a first degree 960 (e.g., the first degree 802 of FIG. 8), relative to the paddle frame 204. For example, elastic deformation of the plurality of compliant mechanisms may include a rotational contraction of each of the plurality of compliant mechanisms, as described with respect to FIGS. 6A-6C. When the imaging system 902 is in the compressed condition 930 and the paddle plate 202 of the flexible paddle 950 is compressing the patient breast 954, the controller of the imaging system may execute a method for imaging the breast.

Following imaging of the breast, the imaging system may be adjusted from the compressed condition 930 to the compression-ready condition 920 to release the patient breast 954 from compression. Movement from the compressed condition 930 to the compression-ready condition 920 includes moving the compression arm assembly 40 in a linear upward movement (e.g., away from the support platform 24). The upward linear movement enables rotational expansion of each of the plurality of compliant mechanisms, which is performed substantially simultaneously with a pivotal movement of the paddle plate 202 back to a substantially horizontal position (e.g., parallel with the paddle frame 204 and the support platform 24. Rotational expansion of the plurality of compliant may be understood herein as relaxation of each of the plurality of compliant mechanisms to a non-elastically deformed, non-contracted configuration. For example, rotational expansion of each of the plurality of compliant mechanisms include increasing a distance between the first end of the compliant mechanism (e.g., coupled to the cutout 402 of the paddle frame 204) and a second end of the compliant mechanism (e.g., coupled to the projection 304 of the paddle plate 202), as described with respect to FIGS. 6A-6C, to equal the distance between the first end and the second end prior to rotational contraction of the plurality of compliant mechanisms.

A technical effect of the present disclosure includes increased accuracy and simplicity in breast positioning, thereby resulting in higher quality x-ray mammography images without repeated and/or increased exposure to the patient. Another technical effect is increased diagnostic capability resulting from accurate breast positioning and thus, reduced instances of repositioning and image recapture. A complexity and a weight of the flex paddle due to the design moving to an injection molded design may decrease, as use of a tilt frame, elastomers, bolts, and so on which are used in current flex paddles are eliminated.

The disclosure also provides support for a flexible paddle for an imaging system, comprising: a paddle frame having a cutout at an end of each of a first arm and a second arm, the cutout extending into a width, perpendicular to a length, of each of the first arm and the second arm, and a paddle plate having a projection positioned in a mid-region of each of a first side and a second side, the projection extending into the respective cutout of the paddle frame and coupled to the paddle frame by a plurality of compliant mechanisms to form a compliant, non-sliding, rotationally-flexible hinge. In a first example of the system, the compliant, non-sliding, rotationally-flexible hinge enables the paddle plate to hinge with respect to the paddle frame and defines an axis of rotation of the paddle plate relative to the paddle frame. In a second example of the system, optionally including the first example, the plurality of compliant mechanisms are elastically deformable. In a third example of the system, optionally including one or both of the first and second examples, each of the plurality of compliant mechanisms extends radially from a body of the projection, the body of the projection extending parallel to a width of the first arm and the second arm of the paddle frame. In a fourth example of the system, optionally including one or more or each of the first through third examples, each of the plurality of compliant mechanisms is a curved extension deformable in two planes. In a fifth example of the system, optionally including one or more or each of the first through fourth examples, each of the plurality of compliant mechanisms is a curved extension between the projection and the cutout of the paddle frame, and the plurality of compliant mechanisms are deformable in one plane. In a sixth example of the system, optionally including one or more or each of the first through fifth examples, each of the plurality of compliant mechanisms is a linear notched extension between the projection and the cutout of the paddle frame, and the plurality of compliant mechanisms are configured to contract and expand in one plane.

The disclosure also provides support for a mammography system, comprising: a support structure, a gantry movably coupled to the support structure, an x-ray source disposed within the gantry, an x-ray detector extending from the support structure, wherein the x-ray detector comprises a support platform, a compression arm assembly movably connected to the gantry substantially between the x-ray source and the x-ray detector, wherein the compression arm assembly is movable between a first linear position distal from the x-ray detector and a second linear position proximate to the x-ray detector, and a flexible paddle removably coupled to the compression arm assembly, the flexible paddle comprising a compliant, non-sliding, rotationally-flexible hinge comprising a paddle plate coupled to a paddle frame by a plurality of compliant mechanisms with elastic deformation. In a first example of the system, the paddle frame comprises: a first arm, a second arm parallel to and spaced apart from the first arm, a cutout at a first end of each of the first arm and the second arm, the cutout extending into a width, perpendicular to a length, of each of the first arm and the second arm, and a cross bar which is perpendicular to and couples the first arm and the second arm at a second end, opposite the first end of the first arm and the second arm. In a second example of the system, optionally including the first example, the cross bar of the paddle frame further comprises a coupling extension which extends in a direction opposite the first arm and the second arm. In a third example of the system, optionally including one or both of the first and second examples, the flexible paddle is coupled to the compression arm assembly via the coupling extension of the paddle frame. In a fourth example of the system, optionally including one or more or each of the first through third examples, the compliant, non-sliding, rotationally-flexible hinge is positioned at the first end of the first arm and the second arm of the paddle frame and in a mid-region of each of a first side and a second side, opposite the first side, of the paddle plate. In a fifth example of the system, optionally including one or more or each of the first through fourth examples, the paddle plate has a bowl shape comprising: a base, a first wall, a second wall opposite the first wall, the second wall having a sloped extension which extends in a direction opposite the first wall, a first side perpendicular to and coupling the first wall and the second wall, a second side, opposite the first side, perpendicular to and coupling the first wall and the second wall, and a projection positioned in a mid-region of and extending perpendicular to each of the first side and the second side away from a center of the paddle plate.

The disclosure also provides support for a method for imaging a breast using an imaging system, comprising: disposing the imaging system in a procedure-ready condition, wherein a flexible paddle is coupled to a compression arm assembly of the imaging system, a paddle plate and a paddle frame of the flexible paddle are substantially horizontal, and the compression arm assembly is a first height above a support platform, moving the imaging system to a compression-ready condition, wherein the paddle plate and the paddle frame are substantially horizontal and the compression arm assembly is disposed at a second height above the support platform, the second height less than the first height, and moving the imaging system to a compressed condition, wherein the compression arm assembly is disposed at a third height, the third height less than the second height, the paddle frame is substantially horizontal, the paddle plate is at least partially in contact with the breast, a plurality of compliant mechanisms coupling the paddle plate to the paddle frame only elastically deformed, and the paddle plate tilted to a first degree relative to the paddle frame. In a first example of the method, during movement to the compressed condition, an elastic deformation of the plurality of compliant mechanisms is performed substantially simultaneously with a pivotal movement of the paddle plate and a linear movement of the compression arm assembly. In a second example of the method, optionally including the first example, the linear movement of the compression arm assembly comprises a downward linear movement of the compression arm assembly. In a third example of the method, optionally including one or both of the first and second examples, the elastic deformation of the plurality of compliant mechanisms includes a rotational contraction of each of the plurality of compliant mechanisms. In a fourth example of the method, optionally including one or more or each of the first through third examples, the method further comprises: moving the imaging system from the compressed condition to the compression-ready condition, wherein movement to the compression-ready condition includes a rotational expansion of each of the plurality of compliant mechanisms which is performed substantially simultaneously with a pivotal movement of the paddle plate and a linear movement of the compression arm assembly. In a fifth example of the method, optionally including one or more or each of the first through fourth examples, the linear movement of the compression arm assembly comprises an upward linear movement of the compression arm assembly. In a sixth example of the method, optionally including one or more or each of the first through fifth examples, the method further comprises: imaging the breast when the imaging system is in the compressed condition.

FIGS. 1-9 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation). FIGS. 2-8 are shown approximately to scale. However, other dimensions may be used if desired.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A flexible paddle for an imaging system, comprising:
   a paddle frame having a cutout at an end of each of a first arm and a second arm, the cutout extending into a width, perpendicular to a length, of each of the first arm and the second arm; and
   a paddle plate having a projection positioned in a mid-region of each of a first side and a second side, the projection extending into the respective cutout of the paddle frame and coupled to the paddle frame by a plurality of compliant mechanisms to form a compliant, non-sliding, rotationally-flexible hinge,
   wherein the plurality of compliant mechanisms directly couples the projection to the cutout within the cutout with no other intervening components.

2. The flexible paddle of claim 1, wherein the compliant, non-sliding, rotationally-flexible hinge enables the paddle plate to hinge with respect to the paddle frame and defines an axis of rotation of the paddle plate relative to the paddle frame, and wherein the paddle plate is stationary along the axis of rotation.

3. The flexible paddle of claim 1, wherein the plurality of compliant mechanisms are elastically deformable.

4. The flexible paddle of claim 1, wherein each of the plurality of compliant mechanisms extends radially from a body of the projection, the body of the projection extending parallel to a width of the first arm and the second arm of the paddle frame.

5. The flexible paddle of claim 1, wherein each of the plurality of compliant mechanisms is a curved extension deformable in two planes.

6. The flexible paddle of claim 1, wherein each of the plurality of compliant mechanisms is a curved extension between the projection and the cutout of the paddle frame, and the plurality of compliant mechanisms are deformable in one plane.

7. The flexible paddle of claim 1, wherein each of the plurality of compliant mechanisms is a linear notched extension between the projection and the cutout of the paddle frame, and the plurality of compliant mechanisms are configured to contract and expand in one plane.

8. A mammography system, comprising:
   a support structure;
   a gantry movably coupled to the support structure;
   an x-ray source disposed within the gantry;
   an x-ray detector extending from the support structure, wherein the x-ray detector comprises a support platform;
   a compression arm assembly movably connected to the gantry substantially between the x-ray source and the x-ray detector, wherein the compression arm assembly is movable between a first linear position distal from the x-ray detector and a second linear position proximate to the x-ray detector; and
   a flexible paddle removably coupled to the compression arm assembly, the flexible paddle comprising a compliant, non-sliding, rotationally-flexible hinge comprising a paddle plate coupled to a paddle frame by a plurality of compliant mechanisms with elastic deformation,
   wherein the paddle frame comprises an outer face and an inner face, and a cutout extending between the outer face and the inner face, wherein the plurality of compliant mechanisms is contained within the cutout between the outer face and the inner face.

9. The mammography system of claim 8, wherein the paddle frame comprises:
   a first arm;
   a second arm parallel to and spaced apart from the first arm;
   the cutout at a first end of each of the first arm and the second arm, the cutout extending into a width, perpendicular to a length, of each of the first arm and the second arm; and
   a cross bar which is perpendicular to and couples the first arm and the second arm at a second end, opposite the first end of the first arm and the second arm.

10. The mammography system of claim 9, wherein the compliant, non-sliding, rotationally-flexible hinge is positioned at the first end of the first arm and the second arm of the paddle frame and in a mid-region of each of a first side and a second side, opposite the first side, of the paddle plate.

11. The mammography system of claim 8, wherein the inner face is parallel with the outer face.

12. The mammography system of claim 8, wherein the paddle plate comprises a projection and the plurality of compliant mechanisms elastically deform about a central axis of rotation that extends through a center of the projection.

13. The mammography system of claim 8, wherein the paddle plate has a bowl shape comprising:
   a base;
   a first wall;
   a second wall opposite the first wall, the second wall having a sloped extension which extends in a direction opposite the first wall;
   a first side perpendicular to and coupling the first wall and the second wall;
   a second side, opposite the first side, perpendicular to and coupling the first wall and the second wall; and
   a projection positioned in a mid-region of and extending perpendicular to each of the first side and the second side away from a center of the paddle plate.

14. A method for imaging a breast using an imaging system, comprising:
   disposing the imaging system in a procedure-ready condition, wherein a flexible paddle is coupled to a compression arm assembly of the imaging system, a paddle plate and a paddle frame of the flexible paddle are substantially horizontal, and the compression arm assembly is a first height above a support platform;
   moving the imaging system to a compression-ready condition, wherein the paddle plate and the paddle frame are substantially horizontal and the compression arm assembly is disposed at a second height above the support platform, the second height less than the first height; and
   moving the imaging system to a compressed condition, wherein the compression arm assembly is disposed at a third height, the third height less than the second height, the paddle frame is substantially horizontal, the paddle plate is at least partially in contact with the breast, a plurality of compliant mechanisms coupling the paddle plate to the paddle frame only elastically deformed, and the paddle plate tilted to a first degree relative to the paddle frame, wherein the paddle frame comprises an outer face, an inner face, and a cutout extending between the outer face and the inner face, and the plurality of compliant mechanisms is contained within the cutout between the outer face and the inner face.

15. The method of claim 14, wherein during movement to the compressed condition, an elastic deformation of the plurality of compliant mechanisms is performed substantially simultaneously with a pivotal movement of the paddle plate and a linear movement of the compression arm assembly.

16. The method of claim 15, wherein the elastic deformation of the plurality of compliant mechanisms includes a rotational contraction of each of the plurality of compliant mechanisms.

17. The method of claim 14, wherein the paddle plate comprises a projection and the plurality of compliant mechanisms elastically deform about a central axis of rotation that extends through a center of the projection, and wherein the plurality of compliant mechanisms is equally distributed about the projection.

18. The method of claim 14, further comprising moving the imaging system from the compressed condition to the compression-ready condition, wherein movement to the compression-ready condition includes a rotational expansion of each of the plurality of compliant mechanisms which is performed substantially simultaneously with a pivotal movement of the paddle plate and a linear movement of the compression arm assembly.

19. The method of claim 18, wherein the linear movement of the compression arm assembly comprises an upward linear movement of the compression arm assembly.

20. The method of claim 14, wherein the paddle plate comprises a projection, wherein a first end of each compliant mechanism is an end adjacent and coupled to one or both of the projection and a receiving body coupled to the projection, and a second end of each compliant mechanism is end adjacent and coupled to an inner wall of the cutout of the paddle frame.

* * * * *